(12) United States Patent
Bleisch et al.

(10) Patent No.: US 6,924,294 B2
(45) Date of Patent: Aug. 2, 2005

(54) EXCITATORY AMINO ACID RECEPTOR ANTAGONISTS

(75) Inventors: Thomas John Bleisch, Noblesville, IN (US); Ana Maria Castano Mansanet, Madrid (ES); Esteban Dominguez-Manzanares, Madrid (ES); Ana Maria Escribano, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 96 days.

(21) Appl. No.: 10/450,669

(22) PCT Filed: Dec. 19, 2001

(86) PCT No.: PCT/US01/45858

§ 371 (c)(1),
(2), (4) Date: Jun. 12, 2003

(87) PCT Pub. No.: WO03/024934

PCT Pub. Date: Mar. 27, 2003

(65) Prior Publication Data

US 2004/0053961 A1 Mar. 18, 2004

(30) Foreign Application Priority Data

Jan. 5, 2001 (EP) .......................................... 01500003

(51) Int. Cl.⁷ ...................... A61K 31/472; C07D 217/16
(52) U.S. Cl. ........................ 514/310; 514/307; 546/146; 546/147
(58) Field of Search .................. 546/146, 147; 514/307, 310

(56) References Cited

U.S. PATENT DOCUMENTS 5,356,902 A   10/1994 Ornstein
5,446,051 A * 8/1995 Ornstein ..................... 514/307
5,767,117 A   6/1998 Moskowitz

FOREIGN PATENT DOCUMENTS

EP        0 590 789    4/1994
WO        WO 98/45270  10/1998
WO        WO 01/01972  1/2001
WO        WO 01/02367  1/2001
WO        WO 01/46173  6/2001

OTHER PUBLICATIONS

Y. Sahara, et al., "Glutamate Receptor Subunits GluR5 and KA–2 Are Coexpressed in Rat Trigeminal Ganglion Neurons," The Journal of Neurosciences, vol. 17, No. 17, pp. 6611–6620 (1997)
Z. Alam, et al., "Plasma levels of neuroexcitatory amino acids in patients with migraine or tension headache," Journal of Neurological Sciences, vol. 156, pp. 102–106 (1998).
Procter, et al., "Possible role of Glu54 glutamate receptors in spinal nociceptive processing in the anaesthetized rat," Journal of Physiology, 504.P, 101P–102P (1997).
Nikam, et al., The search fof AMPA/Gly(N) receptor antagonists: Drugs of the Future, vol. 24, No. 10, pp. 1107–1124 (1999).
Proctor, et al., "Actions of kainite and AMPA selective glutamate receptor ligands on nociceptiv processing in the spinal cord," Neuropharmacology, vol. 37, pp. 1287–1297 (1998).
Bleakman, et al., "Kainate receptor pharmacology and physiology," Cellular and Molecular Life Sciences, 56/7–8 (1999) 558–556.
National Library of Medicine (NLM), Bethesda, MD, US: Mitsilostas, et al., "Non–NMDA glutamate receptors modulate capsaicin induced c–fos expression within trigeminal nucleus caudalis," Database accession No. 10003939 & British Journal of Pharmacology, vol. 127, No. 3, pp. 623–630 (1999).

* cited by examiner

*Primary Examiner*—Ceila Chang
*Assistant Examiner*—Janet L Coppins
(74) *Attorney, Agent, or Firm*—Alexander Wilson

(57) ABSTRACT

The present invention provides novel compounds of Formula (I), or the pharmaceutically acceptable salts or prodrugs thereof, and methods for treating neurological disorders and neurodegenerative diseases, particularly pain and migraine.

44 Claims, No Drawings

EXCITATORY AMINO ACID RECEPTOR ANTAGONISTS

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathways in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). Molecular biological studies have established that AMPA receptors are composed of subunits ($GluR_1$–$GluR_4$), which can assemble to form functional ion channels. Five kainate receptors have been identified which are classified as either High Affinity (KA1 and KA2) or Low Affinity (composed of $GluR_5$, $GluR_6$, and/or $GluR_7$ subunits). Bleakman et al., *Molecular Pharmacology*, 49, No.4, 581,(1996). The second general type of receptor is the G-protein coupled or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, and changes in ion channel function. Schoepp and Conn, *Trends in Pharmacol. Sci.*, 14, 13 (1993). Both types of excitatory amino acid receptor appear not only to mediate normal synaptic transmission along excitatory pathways, but also to participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of neurological disorders and conditions. The medical consequences of such neuronal degeneration makes the abatement of these degenerative neurological processes an important therapeutic goal. For instance, excitatory amino acid receptor excitotoxicity has been implicated in the pathophysiology of numerous neurological disorders, including the etiology of cerebral deficits subsequent to cardiac bypass surgery and grafting, stroke, cerebral ischemia, spinal cord lesions resulting from trauma or inflammation, perinatal hypoxia, cardiac arrest, and hypoglycemic neuronal damage. In addition, excitotoxicity has been implicated in chronic neurodegenerative conditions including Alzheimer's Disease, Huntington's Chorea, inherited ataxias, AIDS-induced dementia, amyotrophic lateral sclerosis, idiopathic and drug-induced Parkinson's Disease, as well as ocular damage and retinopathy. Other neurological disorders implicated with excitotoxicity and/or glutamate dysfunction include muscular spasticity including tremors, drug tolerance and withdrawal, brain edema, convulsive disorders including epilepsy, depression, anxiety and anxiety related disorders such as post-traumatic stress syndrome, tardive dyskinesia, and psychosis related to depression, schizophrenia, bipolar disorder, mania, and drug intoxication or addiction (see generally U.S. Pat. Nos. 5,446,051 and 5,670,516). Excitatory amino acid receptor antagonists may also be useful as analgesic agents and for treating or preventing various forms of headache, including cluster headache, tension-type headache, and chronic daily headache. In addition, published International Patent application WO 98/45720 reports that excitatory amino acid receptor excitotoxicity participates in the etiology of acute and chronic pain states including severe pain, intractable pain, neuropathic pain, post-traumatic pain.

It is also known that trigeminal ganglia, and their associated nerve pathways, are associated with painful sensations of the head and face such as headache and, in particular, migraine. Moskowitz (*Cephalalgia*, 12, 5–7, (1992) proposed that unknown triggers stimulate the trigeminal ganglia which in turn innervate vasculature within cephalic tissue, giving rise to the release of vasoactive neuropeptides from axons innervating the vasculature. These neuropeptides initiate a series of events leading to neurogenic inflammation of the meninges, a consequence of which is pain. This neurogenic inflammation is blocked by sumatriptan at doses similar to those required to treat acute migraine in humans. However, such doses of sumatriptan are associated with contraindications as a result of sumatriptan's attendant vasoconstrictive properties.(see MacIntyre, P. D., et al., *British Journal of Clinical Pharmacology*, 34, 541–546 (1992); Chester, A. H., et al., *Cardiovascular Research*, 24, 932–937 (1990); Conner, H. E., et al., *European Journal of Pharmacology*, 161, 91–94 (1990)). Recently, it has been reported that all five members of the kainate subtype of ionotropic glutamate receptors are expressed on rat trigeminal ganglion neurons, and in particular, high levels of $GluR_5$ and KA2 have been observed. (Sahara et al., *The Journal of Neuroscience*, 17(17), 6611 (1997)). As such, migraine presents yet another neurological disorder which may be implicated with glutamate receptor excitotoxicity.

The use of a neuroprotective agent, such as an excitatory amino acid receptor antagonist, is believed to be useful in treating or preventing all of the aforementioned disorders and/or reducing the amount of neurological damage associated with these disorders. For example, studies have shown that AMPA receptor antagonists are neuroprotective in focal and global ischemia models. The competitive AMPA receptor antagonist NBQX (2,3-dihydroxy-6-nitro-7-sulfamoylbenzo[f]quinoxaline) has been reported effective in preventing global and focal ischemic damage. Sheardown et al., *Science*, 247, 571 (1900); Buchan et al., *Neuroreport*, 2, 473 (1991); LePeillet et al., *Brain Research*, 571, 115 (1992). The noncompetitive AMPA receptor antagonists GKYI 52466 has been shown to be an effective neuroprotective agent in rat global ischemia models. LaPeillet et al., *Brain Research*, 571, 115 (1992). European Patent Application Publication No. 590789A1 and U.S. Pat. Nos. 5,446,051 and 5,670,516 disclose that certain decahydroisoquinoline derivative compounds are AMPA receptor antagonists and, as such, are useful in the treatment of a multitude of disorders conditions, including pain and migraine headache. WO 98/45270 discloses that certain decahydroisoquinoline derivative compounds are selective antagonists of the iGluR$_5$ receptor and are useful for the treatment of various types of pain, including; severe, chronic, intractable, and neuropathic pain.

In accordance with the present invention, Applicants have discovered novel compounds that are antagonists of the iGluR$_5$ receptor subtype and, thus, could be useful in treating the multitude of neurological disorders or neurodegenerative diseases, as discussed above. Such antagonists could address a long felt need for safe and effective treatments for neruological disorders, without attending side effects. The treatment of neurological disorders and neurodegenerative diseases is hereby furthered.

SUMMARY OF THE INVENTION

The present invention provides a compound of Formula I

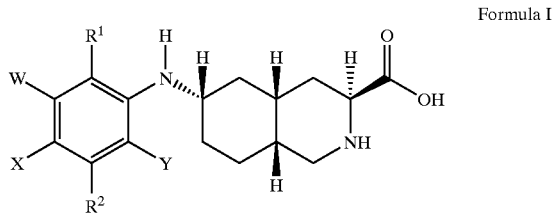

Formula I wherein
R$^1$ is H, CO$_2$H, tetrazole, OH, or (C$_1$–C$_4$)alkyltetrazole;
R$^2$ is H, (C$_1$–C$_6$)alkyl, aryl, halo, CO$_2$H, (C$_1$–C$_6$)alkyl-heterocycle, (C$_1$–C$_6$)alkyl-(substituted)heterocycle, (C$_1$–C$_4$)alkyl-N—SO$_2$-aryl, NO$_2$, NH$_2$, CF$_3$, or (C$_1$–C$_6$)alkoxy carbonyl, NSO$_2$aryl;
W, X, and Y each independently represent H, (C$_1$–C$_6$) alkyl, CO$_2$H, halo, OH, heterocycle, substituted heterocycle, CF$_3$, (CH2)$_n$CO$_2$H, (C$_1$–C$_6$)alkoxy, or (C$_1$–C$_6$)alkoxy carbonyl;
or optionally, X and R$^2$ together, along with the carbon atoms to which they are attached, form a fused-benzo group,
or optionally, W and R$^1$ together, along with the carbon atoms to which they are attached, form a fused-benzo group or a fused-triazole group;
n is 0, 1, or 2,
or a pharmaceutically acceptable salt or prodrug thereof.

In another embodiment, the present invention provides a method of treating or preventing a neurological disorder, or neurodegenerative condition, comprising administering to a patient in need thereof an effective amount of a compound of Formula I or a pharmaceutically acceptable salt thereof. Examples of such neurological disorders, or neurodegenerative conditions, include: cerebral deficits subsequent to cardiac bypass surgery and grafting; stroke; cerebral ischemia; spinal cord lesions resulting from trauma or inflammation; perinatal hypoxia; cardiac arrest; hypoglycemic neuronal damage; Alzheimer's Disease; Huntington's Chorea; inherited ataxias; AIDS-induced dementia; amyotrophic lateral sclerosis; idiopathic and drug-induced Parkinson's Disease; ocular damage and retinopathy; muscular spasticity including tremors; drug tolerance and withdrawal; brain edema; convulsive disorders including epilepsy; depression; anxiety and anxiety related disorders such as post-traumatic stress syndrome; tardive dyskinesia; psychosis related to depression, schizophrenia, bipolar disorder, mania, and drug intoxication or addiction; headache, including cluster headache, tension-type headache, and chronic daily headache; migraine; and acute and chronic pain states including severe pain, intractable pain, neuropathic pain, and post-traumatic pain.

More specifically, the present invention provides a method of treating or preventing pain or migraine comprising administering to a patient in need thereof an effective amount of a compound of Formula I, or a pharmaceutically acceptable salt or prodrug thereof.

In addition, the present invention provides pharmaceutical compositions of compounds of Formula I, including the pharmaceutically acceptable salts, prodrugs, and hydrates thereof, comprising, a compound of Formula I in combination with a pharmaceutically acceptable carrier, diluent or excipient. This invention also encompasses novel intermediates, and processes for the synthesis of the compounds of Formula.

The present invention also provides the use of a compound of Formula I for the manufacture of a medicament for treating or preventing a neurological disorder, or neurodegenerative condition.

More specifically, the present invention provides the use of a compound of Formula I for the manufacture of a medicament for treating or preventing pain or migraine.

DETAILED DESCRIPTION OF THE INVENTION

The present invention provides compounds functional as iGluR$_5$ receptor antagonists as well as pharmaceutically acceptable salts, prodrugs, and compositions thereof. These compounds are useful in treating or preventing neurological disorders, or neurodegenerative diseases, particularly pain and migraine. As such, methods for the treatment or prevention of neurological disorders, or neurodegenerative diseases, are also provided by the present invention.

In addition, it should be understood by the skilled artisan that all of the compounds useful for the methods of the present invention are available for prodrug formulation. As used herein, the term "prodrug" refers to a compound of Formula I which has been structurally modified such that in vivo the prodrug is converted, for example, by hydrolytic, oxidative, reductive, or enzymatic cleavage into the parent compound (e.g. the carboxylic acid (drug), or as the case may be the parent dicarboxylic acid (drug)) as given by Formula I. Such prodrugs may be, for example, metabolically labile mono- or di-ester derivatives of the parent compounds having a carboxylic acid group. It is to be understood that the present invention includes any such prodrugs, such as metabolically labile ester or diester derivatives of compounds of the Formula. In all cases, the use of the compounds described herein as prodrugs is contemplated, and often is preferred, and thus, the prodrugs of all of the compounds provided are encompassed in the names of the compounds herein. Conventional procedures for the selection and preparation of suitable prodrugs are well known to one of ordinary skill in the art.

More specifically, examples of prodrugs of Formula I which are understood to be included within the scope of the present invention, are represented by Formulas Ia below:

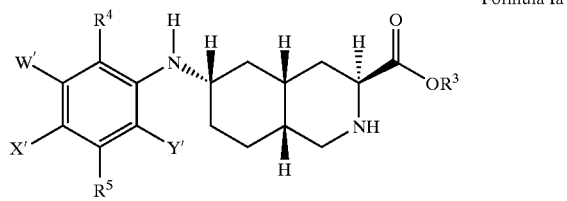

Formula Ia wherein

R³ is hydrogen, ($C_1$–$C_{20}$)alkyl, ($C_2$–$C_6$)alkenyl, ($C_1$–$C_6$) alkylaryl, ($C_1$–$C_6$)alkyl($C_3$–$C_{10}$)cycloalkyl, ($C_1$–$C_6$)alkyl-N,N—$C_1$–$C_6$ dialkylamine, ($C_1$–$C_6$)alkyl-pyrrolidine, ($C_1$–$C_6$)alkyl-piperidine, or ($C_1$–$C_6$)alkyl-morpholine;

R⁴ is H, $CO_2R^6$, tetrazole, OH, or ($C_1$–$C_4$)alkyltetrazole;

R⁵ is H, ($C_1$–$C_6$)alkyl, aryl, halo, $CO_2R^7$, ($C_1$–$C_6$)alkyl-heterocycle, ($C_1$–$C_6$)alkyl-(substituted)heterocycle, ($C_1$–$C_4$) alkyl-N—$SO_2$-aryl, $NO_2$, $NH_2$, $CF_3$, ($C_1$–$C_6$)alkoxy carbonyl, or $NSO_2$aryl;

W', X', and Y' each independently represent H, ($C_1$–$C_6$) alkyl, $CO_2R^8$, halo, OH, heterocycle, substituted heterocycle, $CF_3$, $(CH_2)_nCO_2R^8$, ($C_1$–$C_6$)alkoxy or ($C_1$–$C_6$) alkoxy carbonyl;

R⁶, R⁷, and R⁸ each independently represent hydrogen, ($C_1$–$C_{20}$)alkyl, ($C_2$–$C_6$)alkenyl, ($C_1$–$C_6$)alkylaryl, ($C_1$–$C_6$) alkyl($C_3$–$C_{10}$)cycloalkyl, ($C_1$–$C_6$)alkyl-N,N-$C_1$–$C_6$ dialkylamine, ($C_1$–$C_6$)alkyl-pyrrolidine, ($C_1$–$C_6$)alkyl-piperidine, or ($C_1$–$C_6$)alkyl-morpholine;

or optionally, X' and R⁵ together, along with the carbon atoms to which they are attached, form a benzo-fused group, or optionally, W' and R⁴ together, along with the carbon atoms to which they are attached, form a benzo-fused group or a triazole-fused group, and n is 0, 1, or 2;

with the proviso that where R⁴ is $CO_2R^6$, or R⁵ is $CO_2R^7$, or W', X', or Y' is $CO_2R^8$ then at least one, but no more than two of R³, R⁶, R⁷, and R⁸ is other than hydrogen;

or a pharmaceutically acceptable salt thereof.

It is understood that the iGluR₅ receptor antagonists of the present invention may exist as pharmaceutically acceptable salts and, as such, salts are therefore included within the scope of the present invention. The term "pharmaceutically acceptable salt" as used herein, refers to salts of the compounds provided by, or employed in the present invention which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

It will be understood by the skilled reader that most or all of the compounds used in the present invention are capable of forming salts, and that the salt forms of pharmaceuticals are commonly used, often because they are more readily crystallized and purified than are the free bases. In all cases, the use of the pharmaceuticals described herein as salts is contemplated in the description herein, and often is preferred, and the pharmaceutically acceptable salts of all of the compounds are included in the names of them.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, hydroiodide, dihydroiodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid, mandelic acid, and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred. It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that such salts may exist as a hydrate.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of Formula I can be resolved by one of ordinary skill in the art using standard techniques well known in the art, such as those described by J. Jacques, et al., "Enantiomers, Racemates, and Resolutions", John Wiley and Sons, Inc., 1981.

The compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

The specific stereoisomers and enantiomers of compounds of Formula I can be prepared by one of ordinary skill in the art utilizing well known techniques and processes, such as those disclosed by Eliel and Wilen, "Stereochemistry of Organic Compounds", John Wiley & Sons, Inc., 1994, Chapter 7, Separation of Stereoisomers. Resolution. Racemization, and by Collet and Wilen, "Enantiomers, Racemates, and Resolutions", John Wiley & Sons, Inc., 1981. For example, the specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

As used herein the term "Pg" refers to a suitable nitrogen protecting group. Examples of a suitable nitrogen protecting group as used herein refers to those groups intended to protect or block the nitrogen group against undesirable reactions during synthetic procedures. Choice of the suitable nitrogen protecting group used will depend upon the conditions that will be employed in subsequent reaction steps wherein protection is required, and is well within the knowledge of one of ordinary skill in the art. Commonly used nitrogen protecting groups are disclosed in Greene, "Protective Groups In Organic Synthesis," (John Wiley & Sons, New York (1981)). Suitable nitrogen protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, .alpha.-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, .alpha.,.alpha.-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred suitable nitrogen protecting groups are formyl, acetyl, methyloxycarbonyl, benzoyl, pivaloyl, t-butylacetyl, phenylsulfonyl, benzyl, t-butyloxycarbonyl (Boc) and benzyloxycarbonyl (Cbz).

As used herein the term "$(C_1-C_4)$alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "$(C_1-C_6)$alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like.

As used herein the term "$(C_1-C_{10})$alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like.

As used herein the term "$(C_1-C_{20})$alkyl" refers to a straight or branched, monovalent, saturated aliphatic chain of 1 to 20 carbon atoms and includes, but is not limited to, methyl, ethyl, propyl, isopropyl, butyl, isobutyl, t-butyl, pentyl, isopentyl, hexyl, 3-methylpentyl, 2-ethylbutyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-nonadecyl, n-eicosyl and the like. It is understood that the terms "$(C_1-C_4)$alkyl", "$(C_1-C_6)$alkyl", and "$(C_1-C_{10})$alkyl" are included within the definition of "$(C_1-C_{20})$alkyl".

As used herein, the terms "Me", "Et", "Pr", "iPr", "Bu" and "t-Bu" refer to methyl, ethyl, propyl, isopropyl, butyl and tert-butyl respectively.

As used herein, the term "$(C_1-C_4)$alkoxy" refers to an oxygen atom bearing a straight or branched, monovalent, saturated aliphatic chain of 1 to 4 carbon atoms and includes, but is not limited to methyoxy, ethyoxy, n-propoxy, isopropoxy, n-butoxy, and the like.

As used herein the term "$(C_1-C_6)$alkoxy" refers to an oxygen atom bearing a straight or branched, monovalent, saturated aliphatic chain of 1 to 6 carbon atoms and includes, but is not limited to methoxy, ethoxy, n-propoxy, isopropoxy, n-butoxy, n-pentoxy, n-hexoxy, and the like.

As used herein, the term "$(C_1–C_6)alkyl(C_1–C_6)alkoxy$" refers to a straight or branched, monovalent, saturated aliphatic chain of 1 to 6 carbon atoms which has a $(C_1–C_6)$ alkoxy group attached to the aliphatic chain.

As used herein, the terms "Halo", "Halide" or "Hal" refer to a chlorine, bromine, iodine or fluorine atom, unless otherwise specified herein.

As used herein the term "$(C_2–C_6)alkenyl$" refers to a straight or branched, monovalent, unsaturated aliphatic chain having from two to six carbon atoms. Typical $C_2–C_6$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

As used herein, the term "aryl" refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like. The term "substituted aryl" refers to an aryl group substituted with one or two moieties chosen from the group consisting of halogen, hydroxy, cyano, nitro, $(C_1–C_6)alkyl$, $(C_1–C_4)alkoxy$, $(C_1–C_6)alkyl(C_3–C_{10})cycloalkyl$, $(C_1–C_6)alkylaryl$, $(C_1–C_6)$ alkoxycarbonyl, protected carboxy, carboxymethyl, hydroxymethyl, amino, aminomethyl, or trifluoromethyl.

As used herein, the term "$(C_1–C_6)alkylaryl$" refers to a straight or branched, monovalent, saturated aliphatic chain of 1 to 6 carbon atoms which has an aryl group attached to the aliphatic chain. Included within the term "$C_1–C_6$ alkylaryl" are the following:

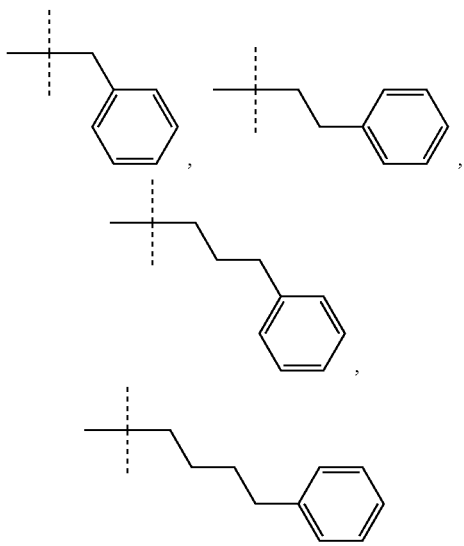

and the like.

As used herein, the term "$aryl(C_1–C_6)alkyl$" refers to an aryl group which has a straight or branched, monovalent, saturated aliphatic chain of 1 to 6 carbon atoms attached to the aryl group. Included within the term "$aryl(C_1–C_6)alkyl$" are the following:

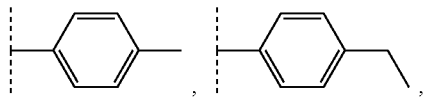

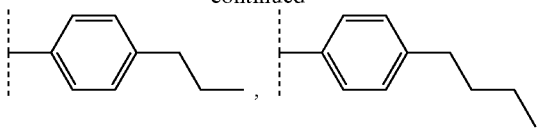

and the like.

As used herein the term "$(C_3–C_{10})cycloalkyl$" refers to a saturated hydrocarbon ring structure composed of one or more fused or unfused rings containing from three to ten carbon atoms. Typical $C_3–C_{10}$ cycloalkyl groups include cyclopropyl, cyclobutyl, cyclopentyl, cyclohexyl, cycloheptyl, cyclooctyl, adamantanyl, and the like.

As used herein, the term "$C_1–C_6$ alkyl$(C_3–C_{10})$cycloalkyl" refers to a straight or branched, monovalent, saturated aliphatic chain of 1 to 6 carbon atoms which has a $(C_3–C_{10})cycloalkyl$ attached to the aliphatic chain. Included within the term "$C_1–C_6$ alkyl$(C_3–C_{10})$cycloalkyl" are the following:

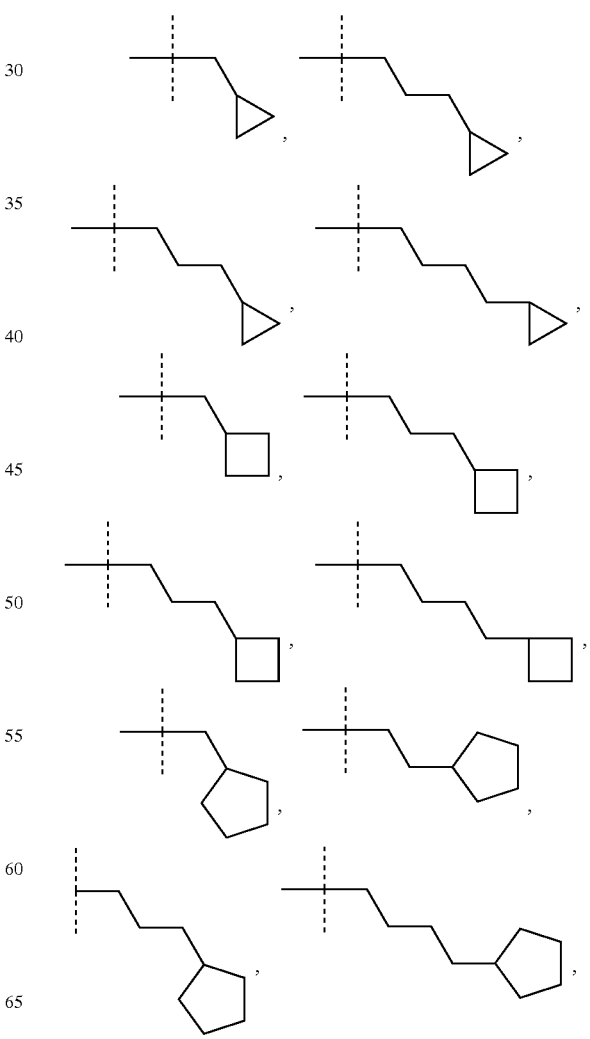

-continued

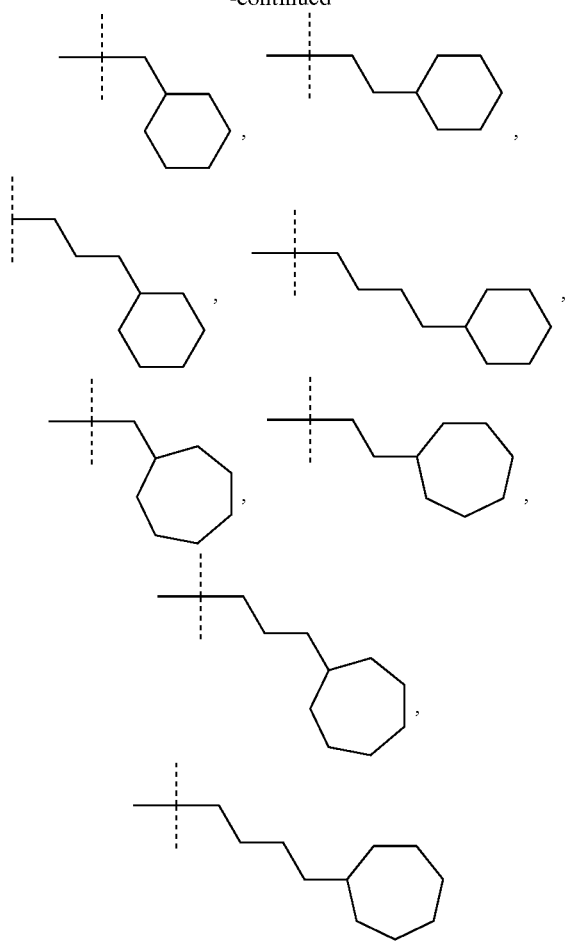

and the like.

As used herein, the term "($C_1$–$C_6$)alkoxycarbonyl" refers to a carbonyl group having a ($C_1$–$C_6$)alkyl group attached to the carbonyl carbon through an oxygen atom. Examples of this group include t-buoxycarbonyl, methoxycarbonyl, and the like.

As used herein the term "heterocycle" refers to a five- or six-membered ring, which contains one to four heteroatoms selected from the group consisting of oxygen, sulfur, and nitorgen. The remaining atoms of the ring are recognized as carbon by those of skill in the art. Rings may be saturated or unsaturated. Examples of heterocycle groups include thiophenyl, furyl, pyrrolyl, imidazolyl, pyrrazolyl, thiazolyl, thiazolidinyl, isothiazolyl, oxazolyl, isoxazolyl, triazolyl, thiadiazolyl, oxadiazolyl, tetrazolyl, pyridyl, pyrimidyl, pyrazinyl, pyridiazinyl, triazinyl, imidazolyl, dihydropyrimidyl, tetrahydropyrimdyl, pyrrolidinyl, piperidinyl, piperazinyl, pyrazolidinyl, pyrimidinyl, imidazolidimyl, morpholinyl, pyranyl, thiomorpholinyl, and the like. The term "substituted heterocycle" represents a heterocycle group substituted with one or two moieties chosen from the group consisting of halogen, hydroxy, cyano, nitro, oxo, aryl, ($C_1$–$C_6$)alkyl, ($C_1$–$C_4$)alkoxy, $C_1$–$C_6$ alkyl($C_3$–$C_{10}$)cycloalkyl, ($C_1$–$C_6$)alkylaryl, ($C_1$–$C_6$) alkoxycarbonyl, protected carboxy, carboxymethyl, hydroxymethyl, amino, aminomethyl, or trifluoromethyl. Further, the heterocycle group can be optionally fused to one or two aryl groups to form a benzo-fused group. Examples of substituted heterocycle include 1,2,3,4-tetrahydrodibenzeofuranyl, 2-methylbezylfuranyl, and 3,5 dimethylisoxazolyl, and the like.

As used herein, the term "($C_1$–$C_6$)alkyl-heterocycle" refers to a straight or branched, monovalent, saturated aliphatic chain of 1 to 6 carbon atoms bearing a heterocycle group. Further, as used herein, the term "($C_1$–$C_6$)alkyl-(substituted)heterocycle" refers to a straight or branched, monovalent, saturated aliphatic chain of 1 to 6 carbon atoms bearing a substituted heterocycle group.

As used herein, the term "($C_1$–$C_6$)alkyltetrazole" refers to a straight or branched, monovalent, saturated aliphatic chain of 1 to 6 carbon atoms bearing a tetrazole group.

As used herein, the term "benzo-fused group" refers to a phenyl group fused to an aromatic radical or a heterocycle group. Included within the term "benzo-fused group" are the following:

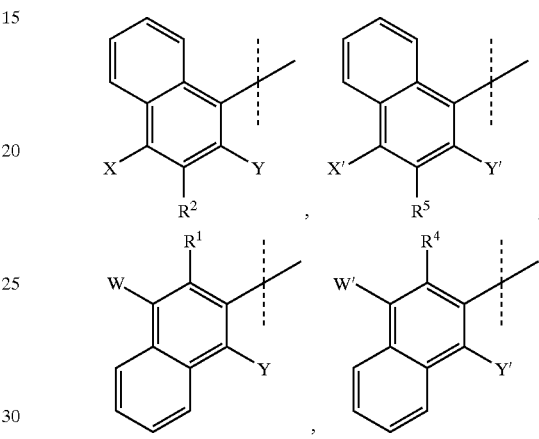

and the like, wherein all substituents are as previously defined hereinabove.

As used herein, the term "triazole-fused group" refers to a triazole group fused to an aromatic radical or a heterocycle group. Included within the term "triazole-fused group" are the following:

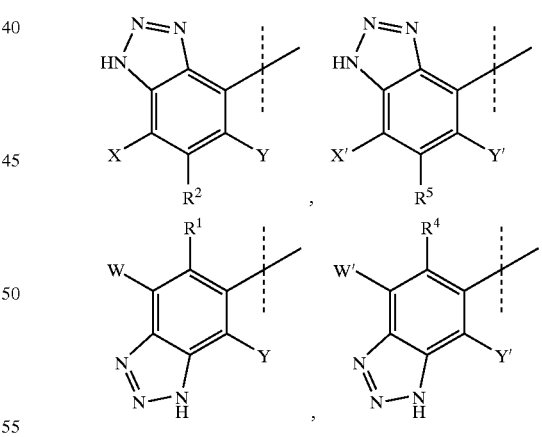

and the like, wherein all substituents are as previously defined.

As used herein the term "N,N—$C_1$–$C_6$ dialkylamine" refers to a nitrogen atom substituted with two straight or branched, monovalent, saturated aliphatic chains of 1 to 6 carbon atoms. Included within the term "N,N—$C_1$–$C_6$ dialkylamine" are —N(CH$_3$)$_2$, —N(CH$_2$CH$_3$)$_2$, —N(CH$_2$CH$_2$CH$_3$)$_2$, —N(CH$_2$CH$_2$CH$_2$CH$_3$)$_2$, and the like.

As used herein the term "$C_1$–$C_6$alkyl-N,N—$C_1$–$C_6$dialkylamine" refers to straight or branched, monovalent, saturated aliphatic chain of 1 to 6 carbon atoms which has an N,N—$C_1$–$C_6$ dialkylamine attached to the aliphatic chain. Included within the term "$C_1$–$C_6$ alkyl-N,N—$C_1$–$C_6$ dialkylamine" are the following:

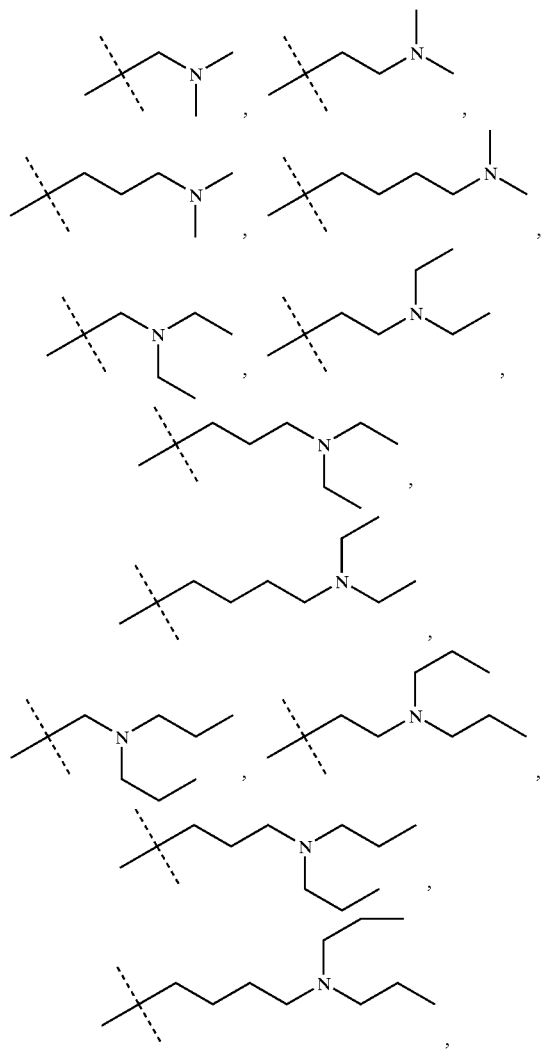

and the like.

As used herein the term "($C_1$–$C_6$)alkyl-pyrrolidine" refers to a straight or branched, monovalent, saturated aliphatic chain of 1 to 6 carbon atoms which has a pyrrolidine attached to the aliphatic chain. Included within the scope of the term "($C_1$–$C_6$)alkyl-pyrrolidine" are the following:

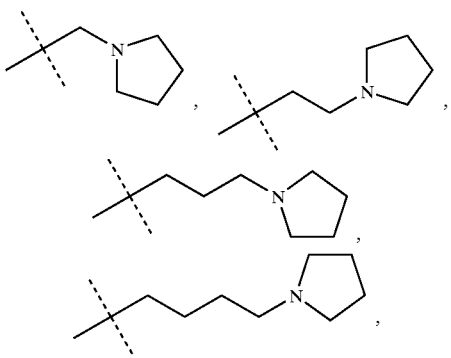

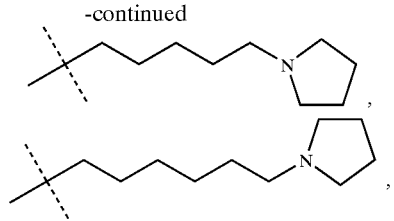

and the like.

As used herein the term "($C_1$–$C_6$)alkyl-piperidine" refers to a straight or branched, monovalent, saturated aliphatic chain of 1 to 6 carbon atoms which has a piperidine attached to the aliphatic chain. Included within the scope of the term "($C_1$–$C_6$)alkyl-piperidine" are the following:

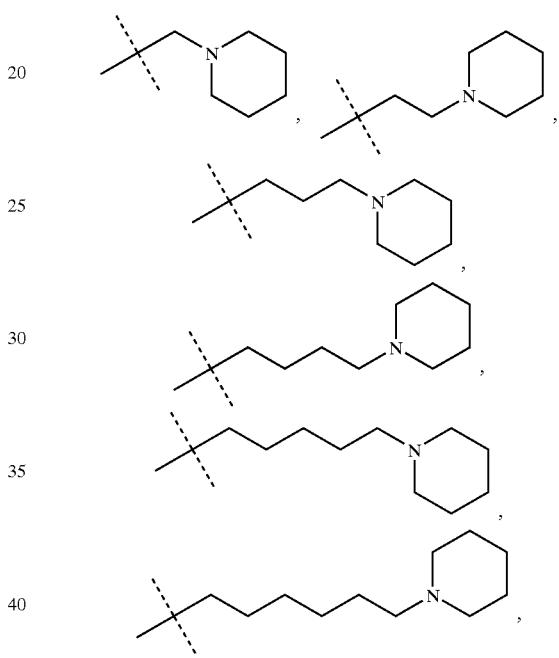

and the like.

As used herein the term "($C_1$–$C_6$)alkyl-morpholine" refers to a straight or branched, monovalent, saturated aliphatic chain of 1 to 6 carbon atoms which has a morpholine attached to the aliphatic chain. Included within the scope of the term "$C_1$–$C_6$ alkyl-morpholine" are the following:

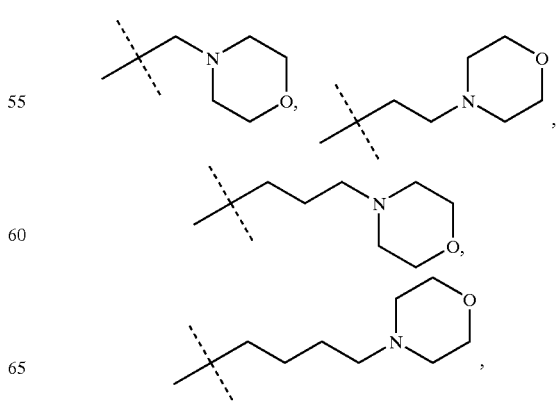

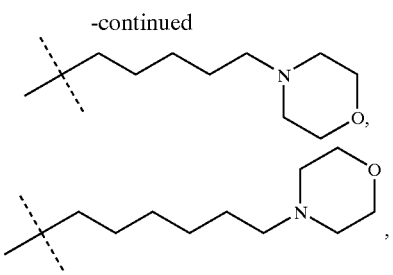

and the like.

The designation "◄" refers to a bond that protrudes forward out of the plane of the page.

The designation "⋯⫼" refers to a bond that protrudes backward out of the plane of the page.

As used herein the term "iGluR₅" refers to the kainate ionotropic glutamate receptor, subtype 5, of the larger class of excitatory amino acid receptors.

As used herein the term "migraine" refers a disorder of the nervous system characterized by recurrent attacks of head pain (which are not caused by a structural brain abnormalitiy such as those resulting from tumor or stroke), gasrointestinal disturbances, and possibly neurological symptoms such as visual distortion. Characteristic headaches of migraine usually last one day and are commonly accompanied by nausea, emesis, and photophobia.

Migraine may represent a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute"means an exacerbated event or attack, of short course, followed by a period of remission. Thus, the treatment of migraine contemplates both acute events and chronic conditions. In an acute event, compound is administered at the onset of symptoms and discontinued when the symptoms disappear. As described above, a chronic condition is treated throughout the course of the disease.

As used herein the term "patient" refers to a mammal, such a mouse, gerbil, guinea pig, rat, dog or human. It is understood, however, that the preferred patient is a human.

The term "iGluR₅ receptor antagonist" or "iGluR₅ antagonist", as used herein, refers to those excitatory amino acid receptor antagonists which bind to, and antagonize the activity of, the iGluR₅ kainate receptor subtype. As a preferred embodiment, the present invention further provides selective iGluR₅ receptor antagonists. "Selective iGluR₅ receptor antagonist" or "selective iGluR₅ antagonist" as used herein, includes those excitatory amino acid receptor antagonists which selectively bind to, and antagonize, the iGluR₅ kainate receptor subtype, relative to the iGluR₂ AMPA receptor subtype. Preferably the "selective iGluR₅ antagonists" for use according to the methods of the present invention have a binding affinity at least 10 fold greater for iGluR₅ than for iGluR₂, more preferably at least 100 fold greater. WO 98/45270 provides examples of selective iGluR₅ receptor antagonists and discloses methods for synthesis.

As used herein, the terms "treating", "treatment", or "to treat" each mean to alleviate symptoms, eliminate the causation of resultant symptoms either on a temporary or permanent basis, and to prevent, slow the appearance, or reverse the progression or severity of resultant symptoms of the named disorder. As such, the methods of this invention encompass both therapeutic and prophylactic administration.

As used herein the term "effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of involvement or the severity of the disease involved; the response of the individual patient; the particular compound administered; the mode of administration; the bioavailability characteristics of the preparation administered; the dose regimen selected; the use of concomitant medication; and other relevant circumstances.

A typical daily dose will contain from about 0.01 mg/kg to about 100 mg/kg of each compound used in the present method of treatment. Preferably, daily doses will be about 0.05 mg/kg to about 50 mg/kg, more preferably from about 0.1 mg/kg to about 25 mg/kg.

Oral administration is a preferred route of administering the compounds employed in the present invention whether administered alone, or as a combination of compounds capable of acting as an iGluR₅ receptor antagonist. Oral administration, however, is not the only route, nor even the only preferred route. Other preferred routes of administration include transdermal, percutaneous, pulmonary, intravenous, intramuscular, intranasal, buccal, sublingual, or intrarectal routes. Where the iGluR₅ receptor antagonist is administered as a combination of compounds, one of the compounds may be administered by one route, such as oral, and the other may be administered by the transdermal, percutaneous, pulmonary, intravenous, intramuscular, intranasal, buccal, sublingual, or intrarectal route, as particular circumstances require. The route of administration may be varied in any way, limited by the physical properties of the compounds and the convenience of the patient and the caregiver.

The compounds employed in the present invention may be administered as pharmaceutical compositions and, therefore, pharmaceutical compositions incorporating compounds of Formula I are important embodiments of the present invention. Such compositions may take any physical form that is pharmaceutically acceptable, but orally administered pharmaceutical compositions are particularly preferred. Such pharmaceutical compositions contain, as an active ingredient, an effective amount of a compound of Formula I, including the pharmaceutically acceptable salts, prodrugs, and hydrates thereof, which effective amount is related to the daily dose of the compound to be administered. Each dosage unit may contain the daily dose of a given compound, or may contain a fraction of the daily dose, such as one-half or one-third of the dose. The amount of each compound to be contained in each dosage unit depends on the identity of the particular compound chosen for the therapy, and other factors such as the indication for which it is given. The pharmaceutical compositions of the present invention may be formulated so as to provide quick, sustained, or delayed release of the active ingredient after administration to the patient by employing well known procedures.

Compositions are preferably formulated in a unit dosage form, each dosage containing from about 1 to about 500 mg of each compound individually or in a single unit dosage form, more preferably about 5 to about 300 mg (for example 25 mg). The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compound, however, is best defined as the "effective amount", that is, the amount of each compound which provides the desired dose to the patient in need of such treatment. The activity of the compounds employed in the present invention do not depend on the nature of the composition, hence, the compositions are chosen and formulated solely for convenience and economy.

Capsules are prepared by mixing the compound with a suitable diluent and filling the proper amount of the mixture in capsules. The usual diluents include inert powdered substances such as starches, powdered cellulose especially crystalline and microcrystalline cellulose, sugars such as fructose, mannitol and sucrose, grain flours, and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

A lubricant is often necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate.

When it is desired to administer the compound as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

The following table provides an illustrative list of formulations suitable for use with the compounds employed in the present invention. The following is provided only to illustrate the invention and should not be interpreted as limiting the present invention in any way.

| Formulation 1 Hard gelatin capsules are prepared using the following ingredients: | |
|---|---|
| | Quantity (mg/capsule) |
| Active Ingredient | 250 |
| Starch, dried | 200 |
| Magnesium stearate | 10 |
| Total | 460 mg |

The above ingredients are mixed and filled into hard gelatin capsules in 460 mg quantities.

| Formulation 2 A tablet is prepared using the ingredients below: | |
|---|---|
| | Quantity (mg/tablet) |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

|  | Weight % |
|---|---|
| Active Ingredient | 0.25 |
| Ethanol | 29.75 |
| Propellant 22 | 70.00 |
| (Chlorodifluoromethane) |  |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient are made as follows:

| Active Ingredient | 60.0 mg |
|---|---|
| Starch | 45.0 mg |
| Microcrystalline cellulose | 35.0 mg |
| Polyvinylpyrrolidone | 4.0 mg |
| Sodium carboxymethyl starch | 4.5 mg |
| Magnesium stearate | 0.5 mg |
| Talc | 1.0 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5
Capsules each containing 80 mg medicament are made as follows:

| Active Ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6
Suppositories each containing 225 mg of active ingredient may be made as follows:

| Active Ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of medicament per 5 ml dose are made as follows:

| Active Ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8
An intravenous formulation may be prepared as follows:

| Active Ingredient | 100 mg |
|---|---|
| Mannitol | 100 mg |
| 5 N Sodium hydroxide | 200 ml |
| Purified water to total | 5 ml |

It is understood by one of ordinary skill in the art that the procedures as described above can also be readily applied to a method of treating neurological disorders or neurodegenerative conditions, particularly pain and migraine, comprising administering to a patient an effective amount of a compound of Formula I.

Compounds of Formula I and Formula Ia can be prepared, for example, by following the procedures set forth in Schemes I and Ia below. All substituents, unless otherwise indicated, are previously defined. The reagents and starting materials are readily available to one of ordinary skill in the art. For example, certain starting materials can be prepared by one of ordinary skill in the art following procedures disclosed in U.S. Pat. No. 5,356,902 (issued Oct. 18, 1994) and U.S. Pat. No. 5,446,051 (issued Aug. 29, 1995) and U.S. Pat. No. 5,670,516 (issued Sep. 23, 1997), the entire contents, all of which are herein incorporated by reference.

Scheme I provides procedures for the synthesis of compounds of Formula I and Formula Ia, wherein $R^1$ represents H, OH, or $CO_2H$, and $R^4$ represents H, OH, or $CO_2R^6$, respectively.

Scheme I

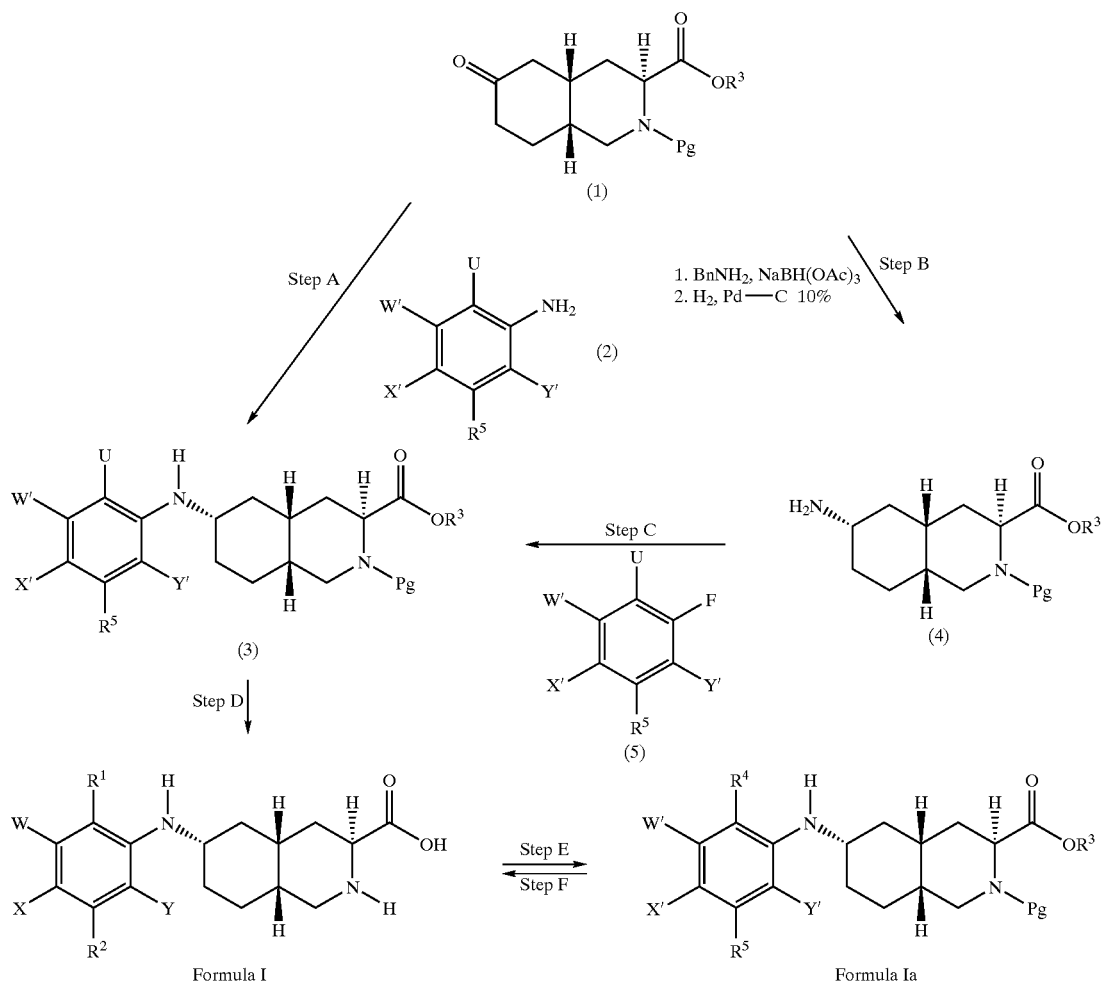

In Scheme I, step A, the compound of structure (1) is treated with a compound of structure (2) (wherein U represents H, OH, or $CO_2R^6$ and $R^5$, W', X', and Y' are as previously defined), under reductive amination conditions, to provide the compound of structure (3). For example, a solution of ethyl 6-oxo-2-(methoxycarbonyl)-decahydroisoquinoline-3-carboxylate dissolved in a suitable organic solvent such as 1,2-dichloroethane at room temperature, is treated with about 0.5–10.0 equivalents of a compound of structure (2) (wherein U represents H, OH, or $CO_2R^6$ and $R^5$, W', X', and Y' are as previously defined) and then the reaction mixture is treated with about 0.5–10.0 equivalents of glacial acetic acid and about 2.0 equivalents of sodium triacethoxyborohydride. The reaction mixture is stirred under nitrogen for about 10 to 48 hours, quenched with sodium bicarbonate until pH 8. The compound of structure (3) (wherein U represents H, OH, or $CO_2R^6$ and $R^5$, W', X', and Y' are as previously defined) is then isolated using standard procedures. For example, after treatment with sodium bicarbonate, the organic layer is separated and the aqueous phase is extracted with ethyl acetate. The combined organic phases are dried over anhydrous sodium sulfate, filtered, and concentrated under vacuum to provide concentrated compound (3). Column chromatography may then be performed on silica gel with a suitable eluent such as 25% ethyl acetate/hexane to provide the purified compound (3).

Alternatively, the compound of structure (3) can be prepared by following the sequence of procedures described in Steps B and C. In Scheme I, Step B, compound (4) is obtained in a two step procedure. First, reductive amination is performed under conditions described above, followed by hydrogenolysis of the resulting benzyl amine to provide the compound of structure (4). For example, a solution of ethyl 6-oxo-2-(methoxycarbonyl)-decahydroisoquinoline-3-carboxylate (compound (1)) dissolved in a suitable organic solvent such as 1,2-dichloroethane at room temperature, is treated with about 1.1 equivalents of $BnNH_2$ (benzyl amine) and then treated with about 1.5 equivalents of glacial acetic acid and about 1.6 equivalents of sodium triacethoxyborohydride. The reaction mixture is stirred under nitrogen at room temperature for about 15 hours and then the reaction mixture is treated with sodium bicarbonate until pH 8, the organic layer separated, and the aqueous phase extracted with ethyl acetate. The combined organic phases are dried over anhydrous sodium sulfate, filtered, and concentrated under vacuum. The resulting crude material is used in the next step without further purification. A mixture of this intermediate dissolved in a suitable organic solvent, such as ethanol, at room temperature is treated with about 0.1 equivalents of 10% palladium on carbon, and hydrogenated at 50 psi at room temperature for about 18 hours. The compound of structure (4) is then isolated using standard procedures. For example, the catalyst is removed by filtration through celite and the solvent evaporated under vacuum to provide the compound of structure (4).

In Scheme I, Step C, compound (4) is treated with a compound of structure (5) (wherein U represents hydrogen, OH, or $CO_2R^6$ and $R^5$, W', X', and Y' are as defined hereinabove) to provide the compound of structure (3). For example, a solution of compound (4) dissolved in a suitable organic solvent such as dimethylsulfoxide, is treated with about 0.2–4.0 equivalents of compound (5) (wherein U represents hydrogen, OH, or $CO_2R^6$ and $R^5$, W', X', and Y' are as defined hereinabove) and then treated with about 1.0 equivalent of sodium bicarbonate. The reaction mixture is heated at 120° C. for 20–70 hours. The compound of structure (3) (as previously defined in Step A) is then isolated using standard procedures. For example, the reaction mixture is treated with ammonium chloride and extract with ethyl acetate, the organic layer is separated and the aqueous phase is extracted with ethyl acetate. The combined organic phases are dried over anhydrous sodium sulfate, filtered, and concentrated under vacuum to provide concentrated compound (3). Column chromatography may then be performed on silica gel with a suitable eluent such as 33% ethyl acetate/hexane to provide the purified compound (3).

In Scheme I, Step D, compound (3) is concomitantly hydrolyzed and deprotected under standard conditions well known in the art to provide the compounds of Formula I, wherein $R^1$, for purposes of this Scheme, represents hydrogen, OH, or $CO_2H$. For example, compound (3) is treated with 6N hydrochloric acid and stirred at 90° C. for 10–24 hours. The mixture is then concentrated under vacuum to provide the compounds of Formula I, wherein $R^1$ represents hydrogen, OH, or $CO_2H$ and $R^2$, W, X, and Y are as previously defined.

In Scheme I, Step E, the compound of Formula I (wherein for purposes of the present Scheme $R^1$ represents hydrogen, OH, or $CO_2H$ and $R^2$, W, X, and Y are as previously defined) may be esterified under standard conditions known in the art to provide the compound of Formula Ia, wherein for purposes of the present Scheme $R^4$ represents hydrogen, OH, or $CO_2R^6$ and $R^3$, $R^5$, W', X', and Y' are as previously defined. For example, the compound of Formula I is dissolved in a suitable base such as 2-ethylbutanol, isobutanol, or ethanol, and treated with an excess of a dehydrating agent, such as thionyl chloride. The reaction mixture is heated at 120° C. for about 2–24 hours. The reaction mixture is then concentrated under vacuum to provide the crude compound of Formula Ia (wherein for purposes of the present Scheme $R^4$ represents hydrogen, OH, or $CO_2R^6$ and $R^3$, $R^5$, W', X', and Y' are as previously defined.) This material may then be precipitated with diethyl ether and filtered to provide the purified compound of Formula Ia.

In Scheme I, Step F, the compound of Formula Ia (wherein for purposes of the present Scheme $R^4$ represents hydrogen, OH, or $CO_2R^6$ and $R^3$, $R^5$, W', X', and Y' are as previously defined) may be hydrolyzed under standard conditions well known in the art to provide the compound of Formula I. For example, the compound of Formula Ia is dissolved in a suitable organic solvent such as methanol, and treated with an excess of a suitable base. Examples of suitable bases include aqueous lithium hydroxide, sodium hydroxide, potassium hydroxide, and the like with lithium hydroxide being preferred. The reaction is stirred for about 10–20 hours. The reaction mixture is then neutralized to pH 6 with 1N HCl and concentrated under vacuum to provide the crude of compound of Formula I, wherein for purposes of the present Scheme $R^1$ represents hydrogen, OH, or $CO_2H$ and $R^2$, W, X, and Y are as previously defined. This material may then be purified by techniques well known in the art, such as cation exchange chromatography eluting with methanol/water followed by 2.0 N ammonia in methanol to provide the purified compound of Formula I.

The compounds of Formula I and Formula Ia, wherein $R^1$ and $R^4$ represent tetrazole or $(C_1-C_4)$alkyltetrazole, may be synthesized according to the procedures as described in Scheme Ia.

Scheme Ia

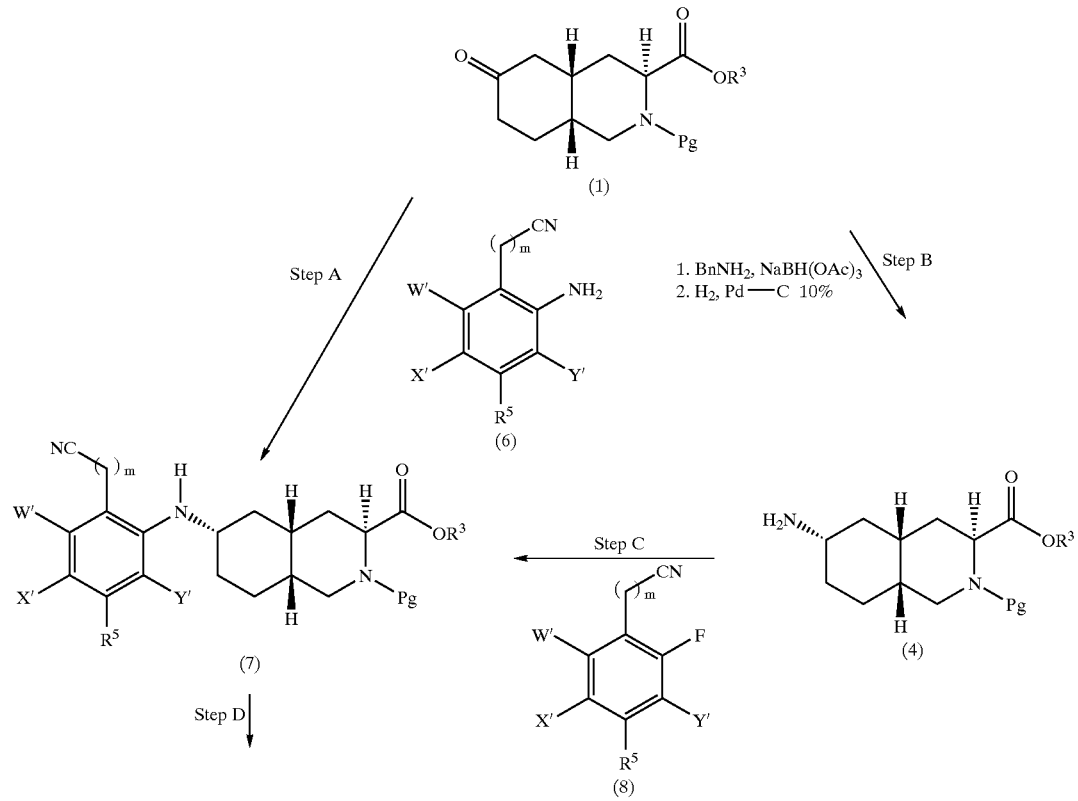

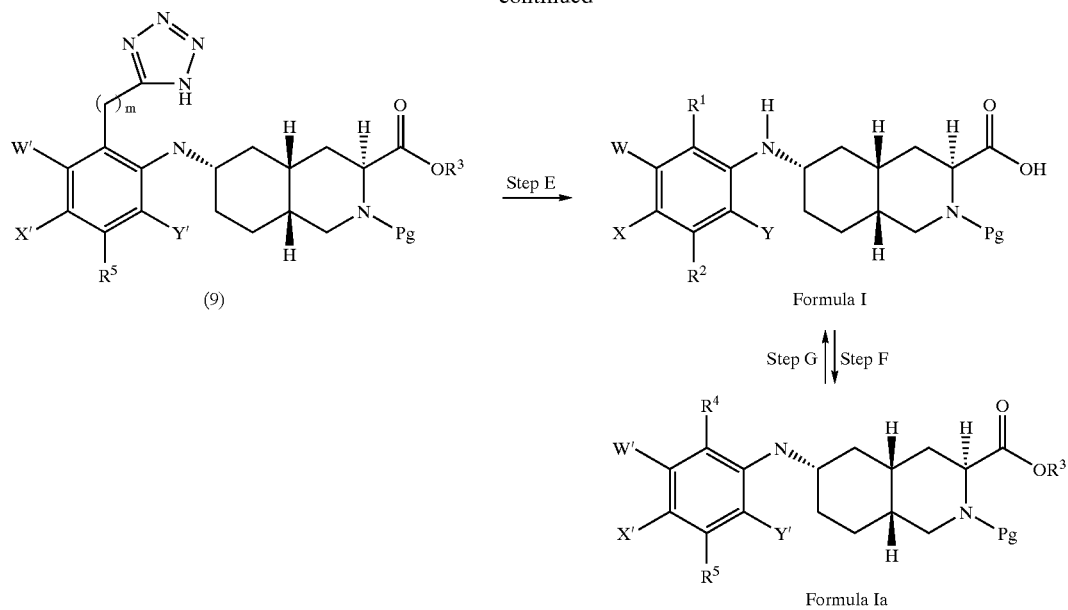

Formula I

Step G ↕ Step F

Formula Ia

In Scheme Ia, step A, following the procedures as described in Scheme I, Step A above, the compound of structure (1) is treated with a compound of structure (6) (wherein for the purposes of the present Scheme CN represents a nitrile group, m=0, 1, 2, 3, or 4, and $R^5$, W', X', and Y' are as previously defined), under reductive amination conditions, to provide the compound of structure (7). The compound (7) is then isolated and concentrated under standard conditions, and may then be purified, all as described in Scheme I, Step A.

Alternatively, the compound of structure (7) can be prepared by following the sequence of procedures described in Steps B and C. In Scheme Ia, Step B, compound (4) is obtained in a two step procedure as previously described in Scheme I, Step B above. The compound of structure (4) is then isolated using standard procedures, again as described in Scheme I, Step B above.

In Scheme Ia, Step C, following the procedures as described in Scheme I, Step C above, compound (4) is treated with a compound of structure (8)(wherein for the purposes of the present Scheme CN represents a nitrile group, m=0, 1, 2, 3, or 4, and $R^5$, W', X', and Y' are as defined hereinabove) to provide the compound of structure (7). The compound of structure (7) is then isolated and concentrated under standard conditions, and may then be purified, all as described in Scheme I, Step C.

Where it is desired that the compound of Formula I or Formula Ia contain a tetrazole or a $(C_1-C_4)$alkyltetrazole at $R^1$, compound (7), wherein CN represents a nitrile and m=0, 1, 2, 3, or 4, is treated with a compound of $Alk_3SnN_3$ (wherein Alk represents an alkyl group such as methyl, ethyl or butyl) in Scheme Ia, Step D to give the compound of structure (9). Compound (9) is then concomitantly hydrolyzed and deprotected in Step E, to provide the compounds of Formula I, wherein $R^1$ is tetrazole or $(C_1-C_4)$ alkyltetrazole. For example, compound (7) is treated with about 3 to 5 equivalents of azido-tri-n-butyl stannane at about 70 to 100° C. for about 12 to 48 hours under an atmosphere of nitrogen to give the compound of structure (9). Compound (9) is then treated with 1N hydrochloric acid, extracted with ethyl acetate, the organic layer separated, and the aqueous phase extracted with ethyl acetate. The combined organic phases are dried over anhydrous sodium sulfate, filtered, and concentrated under vacuum to provide concentrated compound (9). Column chromatography may then be performed on silica gel with a suitable eluent such as 33% ethyl acetate/hexane to provide the purified compound (9). In Scheme Ia, Step E, Compound (9) is then concomitantly hydrolyzed and deprotected under standard conditions well known in the art, and as described in Scheme I, Step D above, and the resulting compound of Formula I (wherein $R^1$ is tetrazole or $(C_1-C_4)$alkyltetrazole) may then be purified. For example, a solution of compound (9) dissolved in 6.0 N hydrochloric acid is heated at 90° C. for 10–24 hours. The reaction mixture is then allowed to cool to room temperature and concentrated under vacuum to provide the compound of Formula I, wherein for the purposes of the present Scheme $R^1$ is tetrazole or $(C_1-C_4)$ alkyltetrazole and $R^2$, W, X, and Y are as previously defined. This material may then be purified by techniques well known in the art, such as cation exchange chromatography eluting with methanol/water followed by 2.0 N ammonia in methanol to provide the purified compound of Formula I.

In Scheme Ia, Step F, following the procedures as described in Scheme I, Step E, the compound of Formula I (wherein for purposes of the present Scheme $R^1$ represents tetrazole or $(C_1-C_4)$alkyltetrazole and $R^2$, W, X, and Y are as previously defined) may be esterified under standard conditions known in the art to provide the compound of Formula Ia, wherein for purposes of the present Scheme $R^4$ represents tetrazole or $(C_1-C_4)$alkyltetrazole and $R^3$, $R^5$, W', X', and Y' are as previously defined. For example, the compound of Formula I is dissolved in a suitable base such as 2-ethylbutanol, isobutanol, or ethanol, and treated with an excess of a dehydrating agent, such as thionyl chloride. The reaction mixture is heated at 120° C. for about 2–24 hours. The reaction mixture is then concentrated under vacuum to provide the crude compound of Formula Ia (wherein for purposes of the present Scheme $R^4$ represents tetrazole or $(C_1-C_4)$alkyltetrazole and $R^3$, $R^5$, W', X', and Y' are as previously defined.) This material may then be precipitated with diethyl ether and filtered to provide the purified compound of Formula Ia.

In Scheme Ia, Step G, the compound of Formula Ia (wherein for purposes of the present Scheme $R^4$ tetrazole or $(C_1-C_4)$alkyltetrazole and $R^3$, $R^5$, W', X', and Y' are as previously defined) may be hydrolyzed under standard conditions well known in the art, and as previously described in Scheme I, Step F above to provide the compound of Formula I. This material may then be purified by techniques well known in the art, such as cation exchange chromatography eluting with methanol/water followed by 2.0 N ammonia in methanol to provide the purified compound of Formula I, wherein $R^4$ tetrazole or $(C_1-C_4)$alkyltetrazole and $R^3$, $R^5$, W', X', and Y' are as previously defined.

The Formula I compounds of the present invention may be chemically synthesized from a common intermediate, a 6-oxo-2-methoxycarbonyl-decahydroisoquinoline-3-carboxylate. This intermediate, in turn, may be synthesized from a 6-oxo-decahydroisoquinoline-3-carboxylic acid, the synthesis of which is described in U.S. Pat. Nos. 4,902,695, 5,446,051, and 5,356,902, the contents of which are all herein incorporated by reference. A route for the synthesis of the 6-oxo-2-methoxycarbonyl-decahydroisoquinoline-3-carboxylate intermediate, useful for the synthesis of the compounds of the present invention, is shown in Scheme II below.

Scheme II

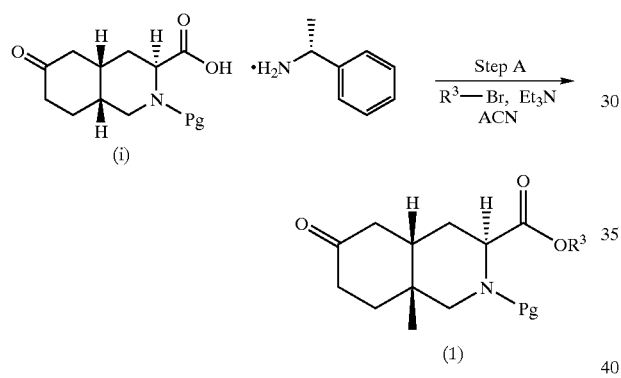

In Scheme II, Step A, 6-oxo-2-(Pg)-decahydroisoquinoline-3-carboxylic acid (Pg is as defined hereinabove) is esterified by reaction with a compound of formula $R^3$—Br (where $R^3$ is as herein defined above) to provide the 6-oxo-2-(Pg)-decahydroisoquinoline-3-carboxylate intermediate of compound (1). For example 6-oxo-2-methoxycarbonyl-decahydroisoquinoline-3-carboxylic acid is dissolved in acetonitrile and treated with tiethylamine and bromoethane. The reaction is heated at 50° C. for about 3 hours, cooled and partitioned between 50:50 ethyl acetate/heptane and 1N HCL. The organic phase is isolated and washed 3 times with water, saturated sodium bicarbonate, brine, dried over anhydrous sodium sulfate, filtered, and concentrated under vacuum to provide Ethyl 6-oxo-2-methoxycarbonyl-decahydroisoquinoline-3-carboxylate, a compound of structure (1). This crude material may then be purified under standard conditions well known in the art. For example, the crude material is dissolved in 10% ethyl acetate/heptane and applied to a plug of silica gel (10 g in 10% ethyl acetate/heptane). The plug is eluted with, 10% ethyl acetate/heptane, 15% ethyl acetate/heptane, and 25% ethyl acetate/heptane. The eluents are combined and concentrated under vacuum to provide the purified compound of structure (1).

The following preparations and examples further illustrate the invention and represent typical synthesis of the compounds of Formula I as described generally above. The reagents and starting materials are readily available to one of ordinary skill in the art. As used herein, the following terms have the meanings indicated: "i.v." refers to intravenously; "p.o." refers to orally; "i.p." refers to intraperitoneally; "eq" or "equiv." refers to equivalents; "g" refers to grams; "mg" refers to milligrams; "L" refers to liters; "mL" refers to milliliters; "$\mu L$" refers to microliters; "mol" refers to moles; "mmol" refers to millimoles; "psi" refers to pounds per square inch; "mm Hg" refers to millimeters of mercury; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "THF" refers to tetrahydrofuran; "DMF" refers to N,N-dimethylformamide; "DMSO" refers to dimethyl sulfoxide; "aq" refers to aqueous; "EtOAc" refers to ethyl acetate; "iPrOAc" refers to isopropyl acetate; "MeOH" refers to methanol; "MTBE" refers to tert-butyl methyl ether; "PPh$_3$" refers to triphenylphosphine; "DEAD" refers to diethyl azodicarboxylate; "RT" refers to room temperature; "Pd—C" refers to palladium over carbon; NaBH(OAc)$_3$ refers to sodium triacetoxyborohydride; "Bn" refers to benzyl; "BnNH$_2$" refers to benzyl amine; H$_2$ refers to hydrogen; "$K_i$" refers to the dissociation constant of an enzyme-antagonist complex and serves as an index of ligand binding; and "ID$_{50}$" and "ID$_{100}$" refer to doses of an administered therapeutic agent which produce, respectively, a 50% and 100% reduction in a physiological response.

PREPARATION 1

Ethyl (3S, 4aR, 6S, 8aR) 6-amino-2-methoxycarbonyl-1,2,3,4,4a,5,6,7,8,8a-decahydroisoquinol-3-carboxylate

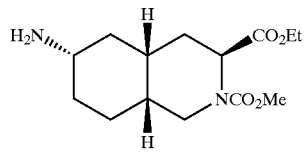

A. Ethyl (3S, 4aR, 6S, 8aR) 6-benzylamino-2-methoxycarbonyl-1,2,3,4,4a,5,6,7,8,8a-decahydroisoquinoline-3-carboxylate.

To a room temperature solution of ethyl 6-oxo-2-methoxycarbonyl-decahydroisoquinoline-3-carboxylate (4 g, 14.1 mmol), benzylamine (1.71 g, 15.9 mmol), and acetic acid (1.27 g, 21.2 mmol) in 1,2-dichloroethane (20 ml), sodium triacetoxyborohydride (5 g, 23.3 mmol) was added. The mixture was stirred under an atmosphere of nitrogen for 15 hours at room temperature. The reaction was quenched by adding aqueous saturated sodium bicarbonate, and extracted with dichloromethane three times. The organic layer was dried over sodium sulfate and evaporated to give 7 g of the title compound. The crude material was used in next step without further purification.

Ion Electrospray Mass Spectrum M+1: 375.

B. Ethyl (3S, 4aR, 6S, 8aR) 6-amino-2-methoxycarbonyl-1,2,3,4,4a,5,6,7,8,8a-decahydroisoquinoline-3-carboxylate.

A mixture of the intermediate from step A above (7 g, 18.7 mmol) and 700 mg of 10% palladium on carbon in 30 mL of ethanol was hydrogenated at 50 psi for 18 hours at room temperature. The catalyst was removed by filtration through celite and the solvent was evaporated under reduced pressure to afford 4 g of the title compound. (Quantitative yield)

1H-NMR (CDCl3, 200.15 MHz): 4.57 (t, J=5.4 Hz, 1H); 4.23–4.12 (m, 2H); 3.69 (s, 3H); 3.69–3.55 (m, 1H); 3.36–3.30 (m, 1H); 3.02 (s, 1H); 2.26–2.02 (m, 3H); 1.77–1.57 (m, 7H); 1.43–1.37 (m, 3H); 1.25 (t, J=7.0 Hz, 3H).

Ion Electrospray Mass Spectrum M+1: 285.

EXAMPLE 1

Preparation of (3S, 4aR, 6S, 8aR) 6-(3-chloro-2-(1(2)H-tetrazol-5-yl)-phenylamino)-1,2,3,4,4a,5,6,7,8, 8a-decahydroisoquinoline-3-carboxylic acid dihydrochloride

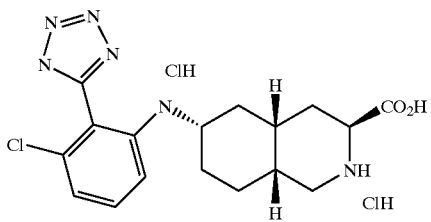

A. Ethyl (3S, 4aR, 6S, 8aR) 6-(3-chloro-2-cyano-phenylamino)-2-methoxycarbonyl-1,2,3,4,4a,5,6,7,8,8a-decahydroisoquinoline-3-carboxylate.

To a mixture of ethyl 6-oxo-2-(methoxycarbonyl)-decahydroisoquinoline-3-carboxylate (142 mg, 0.5 mmol), 2-amino-6-chloro-benzonitrile (760 mg, 5.0 mmol), and glacial acetic acid (0.36 mL, 6.0 mmol) in 1,2-dichloroethane (5 mL), was added 5 g of of 4A molecular sieves (excess of dehydrating agent just to force reaction to completion) and stirred at room temperature overnight under nitrogen. Then, sodium triacethoxyborohydride solid (211 mg, 1.0 mmol) was added and the reaction mixture stirred under nitrogen at room temperature for two days. The reaction mixture was then filtered through celite and sodium bicarbonate was added until pH 8, followed by addition of ethyl acetate. The phases were separated and the aqueous phase washed twice with ethyl acetate. The combined organic phases were dried with anhydrous sodium sulfate and concentrate in vacuo. Flash chromatography (silica gel, hexane-ethyl acetate 3:1) afforded 120 mg (29% yield) of the title compound.

Ion Electrospray Mass Spectrum M+1: 420.

B. Ethyl-(3S, 4aR, 6S, 8aR) 6-(3-chloro-2-(1(2)H-tetrazol-5-yl)-phenylamino)-2-methoxycarbonyl-1,2,3,4,4a,5,6,7,8, 8a-decahydroisoquinoline-3-carboxylate To the product from Example 1A (100 mg, 0.238 mmol), neat azidotributyltin (0.13 mL, 0.477 mmol) was added and heated at 100° C. overnight. 1N HCl (5 mL) was added, followed by extraction with ethyl acetate (2×), dried with anhydrous sodium sulfate, and concentrated in vacuo. Flash chromatography (silica gel, hexane-ethyl acetate-acetic acid 2:1:2%) afforded 62 mg (56% yield) of the title compound.

Ion Electrospray Mass Spectrum M+1: 463.

C. (3S, 4aR, 6S, 8aR) 6-(3-chloro-2-(1(2)H-tetrazol-5-yl)-phenylamino)-1,2,3,4,4a,5,6,7,8,8a-decahydroisoquinoline-3-carboxylic acid dihydrochloride The product from Example 1B (50 mg, 0.108 mmol)was treated with a 6N HCl under reflux overnight. The solution was concentrated in vacuo to afford 34 mg (83% yield) of the title compound.

Ion Electrospray Mass Spectrum M+1: 377.

EXAMPLE 2

Preparation of 2-ethyl-butyl (3S, 4aR, 6S, 8aR) 6-(3-chloro-2-(1(2)H-tetrazol-5-yl)-phenylamino)-1,2,3,4,4a,5,6,7,8,8a-decahydroisoquinoline-3-carboxylate dihydroiodide

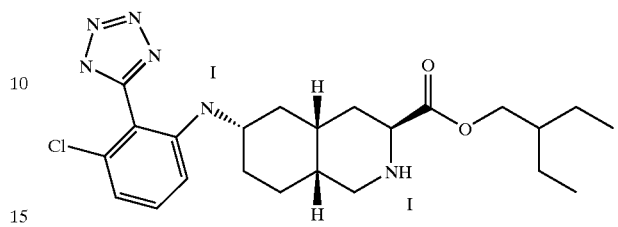

2-ethyl-butyl (3S, 4aR, 6S, 8aR) 6-(3-chloro-2-(1(2)H-tetrazol-5-yl)-phenylamino)-1,2,3,4,4a,5,6,7,8,8a-decahydroisoquinoline-3-carboxylate dihydroiodide is prepared essentially as described for Example 5 herein.

EXAMPLE 3

Preparation of (3S, 4aR, 6S, 8aR) 6-(2-(1(2)H-tetrazol-5-yl)-phenylamino)-1,2,3,4,4a,5,6,7,8,8a-decahydroisoquinoline-3-carboxylic acid dihydrochloride

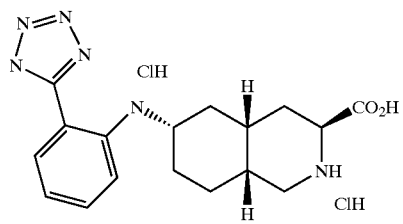

A. Ethyl (3S, 4aR, 6S, 8aR) 6-(2-cyano-phenylamino)-2-methoxycarbonyl-1,2,3,4,4a,5,6,7,8,8a-decahydroisoquinoline-3-carboxylate To a mixture of of ethyl 6-oxo-2-(methoxycarbonyl)-decahydroisoquinoline-3-carboxylate (537 mg, 1.9 mmol), 2-amino-6-chloro-benzonitrile (118 mg, 1.0 mmol), and glacial acetic acid (0.36 mL, 6.0 mmol) in 1,2-dichloroethane (5 mL), sodium triacethoxyborohydride solid (590 mg, 2.8 mmol) was added and the reaction mixture stirred under nitrogen at room temperature for 24 hours. Sodium bicarbonate was added until pH 8, followed by addition of ethyl acetate. The phases were separated and the aqueous phase washed twice with ethyl acetate. The combined organic phases were dried with anhydrous sodium sulfate and concentrated in vacuo. Flash chromatography (silica gel, hexane-ethyl acetate 3:1) afforded 123 mg (32% yield) of the title compound.

Ion Electrospray Mass Spectrum M+1: 384.

B. Ethyl (3S, 4aR, 6S, 8aR) 6-(2-(1(2)H-tetrazol-5-yl)-phenylamino)-2-methoxycarbonyl-1,2,3,4,4a,5,6,7,8,8a-decahydroisoquinoline-3-carboxylate Following the procedures from Example 1B, and using the product from Example 3A (120 mg, 0.31 mmol) neat azidotributyltin (0.17 mL, 0.62 mmol) was added Flash chromatography (silica gel, hexane-ethyl acetate-AcOH 2:1:2%) afforded 80 mg (60% yield) of the title compound.

Ion Electrospray Mass Spectrum M+1: 429.

C. (3S, 4aR, 6S, 8aR) 6-(2-(1(2)H-tetrazol-5-yl)-phenylamino)-1,2,3,4,4a,5,6,7,8,8a-decahydroisoquinoline-3-carboxylic acid dihydrochloride The product from Example 3B (70 mg, 0.164 mmol) was treated following the procedures from Example 1C and afforded 49 mg (87% yield) of the title compound.

Mass Spectrum (Fast Atom Bombardement)M+1: 343.

EXAMPLE 4

Preparation of isobutyl (3S, 4aR, 6S, 8aR)) 6-(2-(1(2)H-tetrazol-5-yl)-phenylamino)-1,2,3,4,4a,5,6,7,8,8a-decahydroisoquinoline-3-carboxylate dihydrochloride

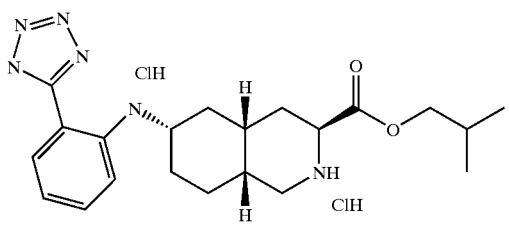

A. Isobutyl alcohol (HCl)

Anhydrous isobutyl alcohol (20 mL) was bubble with HCl (g) for about 5 to 10 min.

B. Isobutyl-(3S, 4aR, 6S, 8aR) 6-(2-(1(2)H-tetrazol-5-yl)-phenylamino)-1,2,3,4,4a,5,6,7,8,8a-decahydroisoquinoline-3-carboxylate dihydrochloride Compound from Example 4A was added to compound from Example 3C (2.0 g, 4.82 mmol) and reflux overnight to afford 2.11 g (93% yield) of the title compound.

Ion Electrospray Mass Spectrum M+1: 472.

EXAMPLE 5

Preparation of 2-ethyl-butyl (3S, 4aR, 6S, 8aR) 6-(2-(1(2)H-tetrazol-5-yl)-phenylamino)-1,2,3,4,4a,5,6,7,8,8a-decahydroisoquinoline-3-carboxylate dihydrochloride

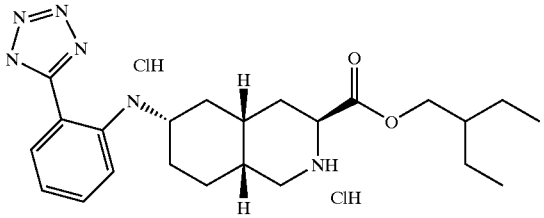

A. 2-Ethyl-1-butanol(HCl)

Anhydrous 2-ethyl-1-butanol (20 mL) was bubble with HCl (g) for about 10 to 15 min.

B. 2-Ethylbutyl (3S, 4aR, 6S, 8aR) 6-(2-(1(2)H-tetrazol-5-yl)-phenylamino)-1,2,3,4,4a,5,6,7,8,8a-decahydroisoquinoline-3-carboxylate dihydrochloride Compound from Example 5A was added to compound from Example 3B (2.0 g, 4.82 mmol) and refluxed overnight to afford 2.09 g (87% yield) of the title compound.

Ion Electrospray Mass Spectrum M+1: 500.

EXAMPLE 6

Preparation of (3S, 4aR, 6S, 8aR) 6-(2-carboxyphenylamino)-1,2,3,4,4a,5,6,7,8,8a-decahydroisoquinoline-3-carboxylic acid

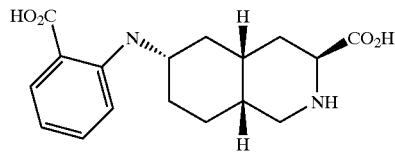

A. Ethyl (3S, 4aR, 6S, 8aR) 6-(2-ethoxycarbonylphenylamino)-2-methoxycarbonyl-1,2,3,4,4a,5,6,7,8,8a-decahydroisoquinoline-3-carboxylate Following the procedure from Example 3A, and using ethyl 6-oxo-2-(methoxycarbonyl)-decahydroisoquinoline-3-carboxylate (537 mg, 1.9 mmol), 2-aminobenzoate (165 mg, 1.0 mmol), glacial acetic acid (0.36 mL, 6.0 mmol), and sodium triacethoxyborohydride (590 mg, 2.8 mmol), flash chromatography (silica gel, hexane-ethyl acetate 3:1) afforded 181 mg (42% yield) of the title compound.

Ion Electrospray Mass Spectrum M+1: 433.

B. (3S, 4aR, 6S, 8aR) 6-(2-carboxyphenylamino)-1,2,3,4,4a,5,6,7,8,8a-decahydroisoquinoline-3-carboxylic acid dihydrochloride Following the procedures from Example 1C, the product from Example 6A (100 mg, 0.232 mmol) afforded 95 mg of a white solid.

C. (3S, 4aR, 6S, 8aR) 6-(2-carboxyphenylamino)-1,2,3,4,4a,5,6,7,8,8a-decahydroisoquinoline-3-carboxylic acid The product from Example 6B (95 mg, 0.24 mmol) was dissolved in water and Dowex resin (2.0 g) was added and stirred for 1 hour. Water was washed away by filtration and the resin washed with 50 mL 1:1 THF/water, then washed with water (50 mL). The resin was collected and a 10% solution of Pyridine-water was added. This was stirred for 2 hours, filtered, and the filtrate collected. The resin was washed with water (10 mL) and the combined pyridine-water filtrate was concentrate in vacuo to afford 51 mg (67% yield) of the title compound as a white solid.

Mass Spectrum (Fast Atom Bombardement)M+1: 319

Analysis calculated for $C_{17}H_{22}N_2O_4 \cdot 2H_2O$: %C, 57.61; %H, 7.39; %N, 7.90. Found %C, 57.82; %H, 7.41; %N, 7.83.

EXAMPLE 7

Preparation of Ethyl (3S, 4aR, 6S, 8aR) 6-(2-ethoxycarbonylphenylamino)-1,2,3,4,4a,5,6,7,8,8a-decahydroisoquinoline-3-carboxylate dihydrochloride

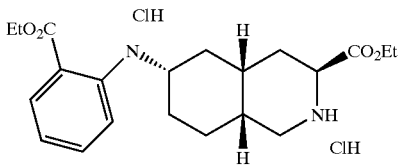

A. Ethanol (HCl)

Anhydrous ethanol (20 mL) was bubble with HCl (g) for about 5 to 10 min.

B. (3S, 4aR, 6S, 8aR) 6-(2-ethoxycarbonylphenylamino)-1,2,3,4,4a,5,6,7,8,8a-decahydroisoquinoline-3-carboxylic acid ethyl ester dihydrochloride Compound from Example 7A was added to compound from Example 6B (2.0 g, 5.1 mmol) and refluxed overnight to afford (2.1 g, 93% yield) of the title compound.

Ion Electrospray Mass Spectrum M+1: 448.

EXAMPLE 8

Preparation of (3S, 4aR, 6S, 8aR) 6-(3-fluoro-2-(1(2)H-tetrazol-5-yl)-phenylamino) 1,2,3,4,4a,5,6,7,8,8a-decahydroisoquinoline-3-carboxylic acid ditrifluoroacetate

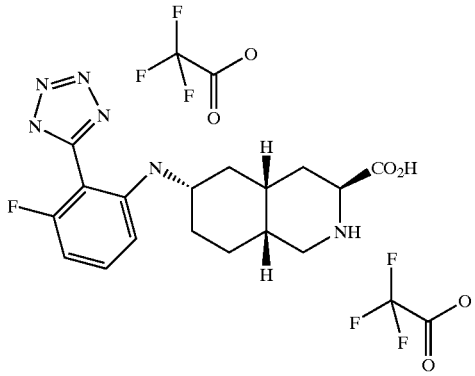

A. Ethyl (3S, 4aR, 6S, 8aR) 6-(3-fluoro-2-cyano-phenylamino)-2-methoxycarbonyl-1,2,3,4,4a,5,6,7,8,8a-decahydroisoquinoline-3-carboxylate Following the procedures from Example 3A, and using 5.38 g (19.0 mmol) of ethyl 6-oxo-2-(methoxycarbonyl)-decahydroisoquinoline-3-carboxylate, 1.36 g (10.0 mmol) of 2-amino-6-fluorobenzonitrile, 3.6 mL (60 mmol) of glacial acetic acid, 5.7 g (27.0 mmol) of sodium triacetoxyborohydride, flash chromatography (silica gel, hexane-ethyl acetate 3:1) afforded 50 mg (1% yield) of the title compound.

Ion Electrospray Mass Spectrum M+1: 404.

B. (3S, 4aR, 6S, 8aR) 6-(3-fluoro-2-(1(2)H-tetrazol-5-yl)-phenylamino) 1,2,3,4,4a,5,6,7,8,8a-decahydroisoquinoline-3-carboxylic acid ditrifluoroacetate To the product from Example 8A (50 mg, 0.124 mmol) was added neat azidotributyltin (0.068 mL, 0,248 mmol) and the reaction heated at 100° C. overnight. A 6N HCl solution was added and heated at the same temperature for 24 hours, followed by extraction with ethyl ether (2x). The aqueous phase was concentrate in vacuo to afford the title compound as dihydrochloride. This crude material was purified by HPLC (using as eluent a gradient of acetonitrile-1% TFA and water) to afford 15 mg (3%) of the title compound

EXAMPLE 9

Preparation of (3S, 4aR, 6S, 8aR) 6-(5-phenyl-2-(1(2)H-tetrazol-5-yl)-phenylamino) 1,2,3,4,4a,5,6,7,8,8a-decahydroisoquinoline-3-carboxylic acid dihydrochloride

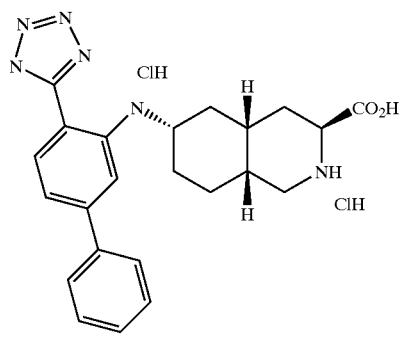

A. 3-Fluoro-biphenyl-4-carbonitrile

To a solution of 4-bromo-2-fluorobenzonitrile (1.12 g, 5.6 mmol) in 1,2-dimethoxyethane (10 mL) were added Phenyl boronic acid (750 mg, 6.16 mmol), tetrakis(triphenylphosphine)palladium (0) (194 mg, 0.17 mmol) and Cesium fluoride (1.8 g, 12.3 mmol). The mixture of reaction was stirred at 100° C. under nitrogen for 3 h. Then, the mixture is cooled and filter through celite. Then added ethyl acetate and water and extracted (3x). The crude was purified by chromatography (silica gel, hexane-ethyl acetate 10:1) affordind 818 mg (74% yield)n of the title compound.

B. Ethyl (3S, 4aR, 6S, 8aR) 6-(2-cyano-5-phenyl-phenylamino)-2-methoxycarbonyl-1,2,3,4,4a,5,6,7,8,8a-decahydroisoquinoline-3-carboxylate To a mixture of the intermediate from preparation 1 (426 mg, 1.5 mmol) and the product from 9A (100 mg, 0.5 mmol) in DMSO (2 mL) was added powdered NaHCO₃ (100 mg, 1.0 mmol) and the reaction mixture heated at 120° C. for 70 h. Then, a saturated solution of NH₄Cl was added and extracted with ethyl acetate (2x), dried, and concentrated in vacuo. Flash chromatography (silica gel, hexane-ethyl acetate 2:1) afforded 125 mg (55% yield) of the title product.

Ion Electrospray Mass Spectrum M+1: 462.

C. Ethyl (3S, 4aR, 6S, 8aR) 6-(4-phenyl-2-(1(2)H-tetrazol-5-yl)-phenylamino)-2-methoxycarbonyl-1,2,3,4,4a,5,6,7,8,8a-decahydroisoquinoline-3-carboxylate Following the procedures from Example 1B, and using the product from Example 9B(125 mg, 0.27 mmol) and neat azidotributyltin (150 mL, 0.54 mmol), flash chromatography (silica gel, hexane-ethyl acetate-acetic acid 2:1:2%) afforded 95 mg (70% yield) of the title compound.

Ion Electrospray Mass Spectrum M+1: 505.

D. (3S, 4aR, 6S, 8aR) 6-(5-phenyl-2-(1(2)H-tetrazol-5-yl)-phenylamino) 1,2,3,4,4a,5,6,7,8,8a-decahydroisoquinoline-3-carboxylic acid dihydrochloride Following the procedures from Example 1C, and using the product from Example 9C (90 mg, 0.18 mmol) afforded 60 mg (75% yield) of the title compound Ion Electrospray Mass Spectrum M+1: 419.

EXAMPLE 10

Preparation of (3S, 4aR, 6S, 8aR) 6-(2-Carboxy-4-fluoro-phenylamino)-1,2,3,4,4a,5,6,7,8,8a-decahydroisoquinoline-3-carboxylic acid dihydrochloride

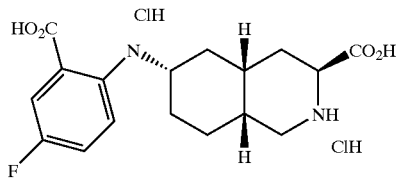

A. Ethyl (3S, 4aR, 6S, 8aR) 6-(2-ethoxycarbonyl-4-fluoro-phenylamino)-2-methoxycarbonyl-1,2,3,4,4a,5,6,7,8,8a-decahydroisoquinoline-3-carboxylate Following the procedures from Example 1A, and using ethyl 6-oxo-2-(methoxycarbonyl)-decahydroisoquinoline-3-carboxylate (537 mg, 1.9 mmol), 2-amino-5-fluoro-benzoic acid ethyl ester (183 mg, 1.0 mmol), glacial acetic acid (0.36 mL, 6.0 mmol), and sodium triacetoxyborohydride (590 mg, 2.8 mmol), flash chromatography (silica gel, hexane-ethyl acetate 3:1) afforded 95 mg (22% yield) of the title compound.

Ion Electrospray Mass Spectrum M+1: 431.

B. (3S, 4aR, 6S, 8aR) 6-(2-carboxy-4-fluoro-phenylamino)-1,2,3,4,4a,5,6,7,8,8a-decahydroisoquinoline-3-carboxylic acid dihydrochloride Following the procedures from Example 1C, and using the product from Example 10A (90 mg, 0.21 mmol), 45 mg (50% yield) of the title compound was afforded.

Ion Electrospray Mass Spectrum M+1: 364.

EXAMPLE 11

Preparation of (3S, 4aR, 6S, 8aR) 6-(5-methyl-2-(1(2)H-tetrazol-5-yl)-phenylamino)-1,2,3,4,4a,5,6,7,8,8a-decahydroisoquinoline-3-carboxylic acid ditrifluoroacetate

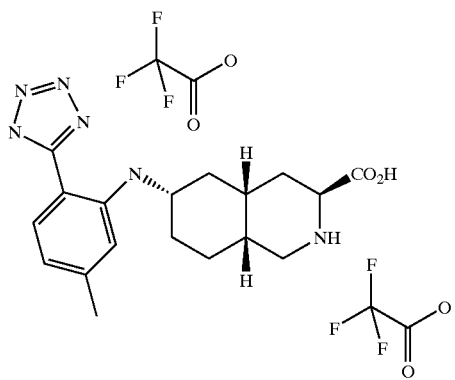

A. Ethyl (3S, 4aR, 6S, 8aR) 6-(2-cyano-5-methyl-phenylamino)-2-methoxycarbonyl-1,2,3,4,4a,5,6,7,8,8a-decahydroisoquinoline-3-carboxylate Following the procedures from Example 3A, and using 1.076 g (3.8 mmol) of ethyl 6-oxo-2-(methoxycarbonyl)-decahydroisoquinoline-3-carboxylate, 1.36 g (10.0 mmol) of 2-amino-5-methylbenzonitrile, 0.67 mL (12 mmol) of glacial acetic acid, and 1.14 g (5.4 mmol) of sodium triacetoxyborohydride, flash chromatography (silica gel, hexane-ethyl acetate 3:1) afforded 80 mg (10% yield) of the title compound.

Ion Electrospray Mass Spectrum M+1: 416.

B. (3S, 4aR, 6S, 8aR) 6-(5-methyl-2-(1(2)H-tetrazol-5-yl)-phenylamino) 1,2,3,4,4a,5,6,7,8,8a-decahydroisoquinoline-3-carboxylic acid ditrifluoroacetate Following the procedures from Example 8B, and using the product from Example 11A (80 mg, 0.193 mmol) and azidotributyltin (0.105 mL, 0.385 mmol), 10 mg (1%) of the title compound was afforded.

Ion Electrospray Mass Spectrum M+1: 357.

EXAMPLE 12

Preparation of (3S, 4aR, 6S, 8aR) 6-(3-methyl-2-(1(2)H-tetrazol-5-yl)-phenylamino)-1,2,3,4,4a,5,6,7,8,8a-decahydroisoquinoline-3-carboxylic acid ditrifluoroacetate

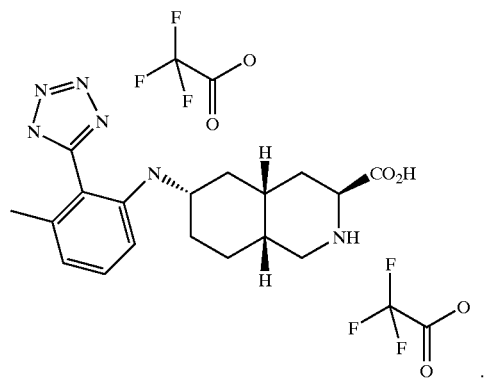

A. Ethyl (3S, 4aR, 6S, 8aR) 6-(2-cyano-3-methyl-phenylamino)-2-methoxycarbonyl-1,2,3,4,4a,5,6,7,8,8a-decahydroisoquinoline-3-carboxylate Following the procedures from Example 3A, and using 1.076 g (3.8 mmol) of ethyl 6-oxo-2-(methoxycarbonyl)-decahydroisoquinoline-3-carboxylate, 1.36 g (10.0 mmol) of 2-amino-5-methylbenzonitrile, 0.67 mL (12 mmol) of glacial acetic acid, and 1.14 g (5.4 mmol) of sodium triacetoxyborohydride, flash chromatography (silica gel, hexane-ethyl acetate 3:1) afforded 105 mg (13% yield) of the title compound.

Ion Electrospray Mass Spectrum M+1: 416.

B. (3S, 4aR, 6S, 8aR) 6-(3-methyl-2-(1(2)H-tetrazol-5-yl)-phenylamino) 1,2,3,4,4a,5,6,7,8,8a-decahydroisoquinoline-3-carboxylic acid dichloro hydrate Following the procedures from Example 8B, and using the product from Example 12A (100 mg, 0.241 mmol) and azidotributyltin (0.1132 mL, 0.482 mmol), 8 mg (1%) of the title compound was afforded.

Ion Electrospray Mass Spectrum M+1: 357.

EXAMPLE 13

Preparation of (3S, 4aR, 6S, 8aR) 6-(3-carboxy-phenylamino)-1,2,3,4,4a,5,6,7,8,8a-decahydroisoquinoline-3-carboxylic acid dichlorohydride

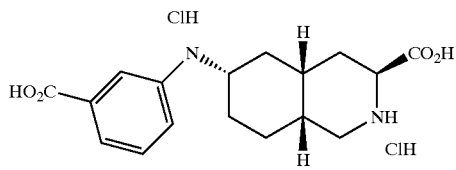

A. Ethyl (3S, 4aR, 6S, 8aR) 6-(3-ethoxycarbonylphenylamino)-2-methoxycarbonyl-1,2,3,4,4a,5,6,7,8,8a-decahydroisoquinoline-3-carboxylate Following the procedures from Example 1A, and using ethyl 6-oxo-2-(methoxycarbonyl)-decahydroisoquinoline-3-carboxylate (11.4 g, 40.28 mmol), 3-aminobenzoic acid ethyl ester (3.5 g, 21.2 mmol), glacial acetic acid (5.0 mL, 84.0 mmol), and sodium triacethoxyborohydride (12.58 g, 59.36 mmol) flash chromatography (silica gel, hexane-ethyl acetate 3:1) afforded 8.35 g (92% yield) of the title compound.

Ion Electrospray Mass Spectrum M+1: 433.

B. (3S, 4aR, 6S, 8aR) 6-(3-carboxy-phenylamino)-1,2,3,4,4a,5,6,7,8,8a-decahydroisoquinoline-3-carboxylic acid dichlorohydride Following the procedures from Example 1C, and using the compound from Example 13A (2.7 g, 6.25 mmol) afforded 2.4 g (98% yield) of the title compound Ion Electrospray Mass Spectrum M+1: 319.

Analysis calculated for $C_{17}H_{24}Cl_2N_2O_4H_2O$: %C, 49.89; %H, 6.40; %N, 6.84. Found %C, 50.03; %H, 6.28; %N, 6.79.

EXAMPLE 14

Preparation of Ethyl (3S, 4aR, 6S, 8aR) 6-(3-ethoxycarbonyl-phenylamino)-1,2,3,4,4a,5,6,7,8,8a-decahydroisoquinoline-3-carboxylic acid, dihydrochloride

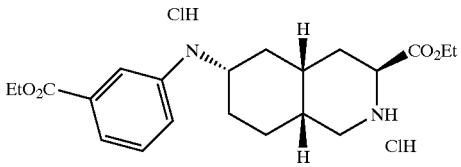

The compound from Example 13 (2.3 g, 5.88 mmol) was treated with ethanol saturated with HCl and refluxed overnight. Concentration in vacuo afforded 2.37 g (90% yield) of the title compound Ion Electrospray Mass Spectrum M+1: 375.

EXAMPLE 15

To establish that the $iGluR_5$ receptor subtype is mediating a pharmacological response in a neurological disease or disorder, the binding affinity of the panel compounds to the $iGluR_5$ receptor is first measured using standard methods. For example, the activity of compounds acting at the $iGluR_5$ receptor can be determined by radiolabelled ligand binding studies at the cloned and expressed human iGluR5 receptor (Korczak et al., 1994, Recept. Channels 3; 41–49), and by whole cell voltage clamp electrophysiological recordings of currents in acutely isolated rat dorsal root ganglion neurons (Bleakman et al., 1996, Mol. Pharmacol. 49; 581–585). The selectivity of compounds acting at the $iGluR_5$ receptor subtype can then be determined by comparing antagonist activity at the $iGluR_5$ receptor with antagonist activity at other AMPA and kainate receptors. Methods useful for such comparison studies include: receptor-ligand binding studies and whole-cell voltage clamp electrophysiological recordings of functional activity at human $GluR_1$, $GluR_2$, $GluR_3$ and $GluR_4$ receptors (Fletcher et al., 1995, Recept. Channels 3; 21–31); receptor-ligand binding studies and whole-cell voltage clamp electrophysiological recordings of functional activity at human $GluR_6$ receptors (Hoo et al., Recept. Channels 2;327–338); and whole-cell voltage clamp electrophysiological recordings of functional activity at AMPA receptors in acutely isolated cerebellar Purkinje neurons (Bleakman et al., 1996, Mol. Pharmacol. 49; 581–585) and other tissues expressing AMPA receptors (Fletcher and Lodge, 1996, Pharmacol. Ther. 70; 65–89).

$iGluR_5$ Antagonist Binding Affinity Profiles

Cell lines (HEK293 cells) stably transfected with human iGluR receptors are employed. Displacement of $^3[H]$ AMPA by increasing concentrations of antagonist is measured on $iGluR_1$, $iGluR_2$, $iGluR_3$, and $iGluR_4$ expressing cells, while displacement of $^3[H]$ kainate (KA) is measured on $iGluR_5$, $iGluR_6$, $iGluR_7$, and KA2-expressing cells. Estimated antagonist binding activity ($K_i$) in $\mu M$, for example, is determined for Compounds of Formula I. As an indicia of selectivity, the ratio of binding affinity to the $iGluR_2$ AMPA receptor subtype, versus the binding affinity to $iGluR_5$ kainate receptor subtype ($K_i$ at $iGluR_2/K_i$ at iGluR5) is also determined. The iGluR5 receptor antagonist compounds, as provided by the present invention, provide a $K_i$ at the iGluR5 receptor subtype of less than 5000 $\mu M$, preferably less than 500 $\mu M$, even more preferably less than 50 $\mu M$, and most preferably less than 5 $\mu M$. The preferred selective iGluR5 receptor antagonists compounds, as provided by the present invention, display a greater binding affinity (lower $K_i$) for $iGluR_5$ than that for $iGluR_2$, preferably at least 10 fold greater for $iGluR_5$ than that for $iGluR_2$, and even more preferably at least 100 fold, and most preferably at least 1000 fold. than that for $iGluR_2$.

EXAMPLE 16

The following animal model may be employed to determine the ability of each of the compounds of Formula I to inhibit protein extravasation, an exemplary functional assay of the neuronal mechanism of migraine.

Animal Model of Dural Protein Extravasation

Harlan Sprague-Dawley rats (225–325 g) or guinea pigs from Charles River Laboratories (225–325 g) are anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes are drilled through the skull (6 mm posterially, 2.0 and 4.0 mm laterally in rats; 4 mm posteriorly and 3.2 and 5.2 mm laterally in guinea pigs, all coordinates referenced to bregma). Pairs of stainless steel stimulating electrodes, insulated except at the tips (Rhodes Medical Systems, Inc.), are lowered through the holes in both hemispheres to a depth of 9 mm (rats) or 10.5 mm (guinea pigs) from dura.

The femoral vein is exposed and a dose of the test compound is injected intravenously (i.v.) at a dosing volume of 1 ml/Kg or, in the alternative, test compound is administered orally (p.o) via gavage at a volume of 2.0 ml/Kg. Approximately 7 minutes post i.v. injection, a 50 mg/Kg dose of Evans Blue, a fluorescent dye, is also injected intravenously. The Evans Blue complexes with proteins in the blood and functions as a marker for protein extravasation. Exactly 10 minutes post-injection of the test compound, the left trigeminal ganglion is stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals are euthanized by exsanguination with 20 mL of saline. The top of the skull is removed to facilitate the collection of the dural membranes. The membrane samples are removed from both hemispheres, rinsed with water, and spread flat on microscopic slides. Once dried, the tissues are coverslipped with a 70% glycerol/water solution.

A fluorescence microscope (Zeiss) equipped with a grating monchromator and a spectrophotometer is used to quantify the amount of Evans Blue dye in each sample. An excitation wavelength of approximately 535 nm is utilized and the emission intensity at 600 nm is determined. The microscope is equipped with a motorized stage and also interfaced with a personal computer. This facilitates the computer-controlled movement of the stage with fluorescence measurements at 25 points (500 mm steps) on each dural sample. The mean and standard deviation of the measurements are determined by the computer.

The extravasation induced by the electrical stimulation of the trigeminal ganglion has an ipsilateral effect (i.e. occurs only on the side of the dura in which the trigeminal ganglion was stimulated). This allows the other (unstimulated) half of the dura to be used as a control. The ratio ("extravasation ratio") of the amount of extravasation in the dura from the stimulated side, over the amount of extravasation in the unstimulated side, is calculated. Control animals dosed with only with saline, yield an extravasation ratio of approximately 2.0 in rats and approximately 1.8 in guinea pigs. In contrast, a compound which completely prevents the extravasation in the dura from the stimulated side would yield a ratio of approximately 1.0.

Dose-response curves are generated for each of the compounds of Formula I and the dose that inhibits the extravasation by 50% ($ID_{50}$) or 100% ($ID_{100}$) is approximated.

EXAMPLE 17

To demonstrate the utility of compounds of the present invention to treat pain or provide analgesic effects, several well known animal models may be employed. For example, international application WO 98/45270 describes the well known Formalin Test, which is described below:

Formalin Test

For example, male Sprague-Dawley rats (200–250 g; Charles River, Portage, Mich.) are housed in group cages and maintained in a constant temperature and a 12 hour light/12 hour dark cycle 4–7 days before studies are performed. Animals have free access to food and water at all times prior to the day of the experiment.

Drugs or vehicles are administered intraperitoneally (i.p.) or orally (p.o.) by gavage in a volume of about 1 ml/kg. The test is performed in custom made Plexiglas® boxes about 25×25×20 cm in size (according to Shibata et al., Pain 38;347–352, 1989, Wheeler-Aceto et al., Pain, 40; 229–238, 1990). A mirror placed at the back of the cage allows the unhindered observation of the formalin injected paw. Rats are acclimated individually in the cubicles at least 1 hour prior to the experiment. All testing is conducted between, for example, 08:00 and 14:00 h and the testing room temperature is maintained at about 21–23° C.

Test compounds are administered about 30 minutes prior to the formalin injection. Formalin (50 micoliters of a 5% solution in saline) is injected subcutaneously into the dorsal lateral surface of the right hind paw with a 27 gauge needle. Observation is started immediately after the formalin injection. Formalin-induced pain is quantified by recording, for example, in 5 minute intervals, the number of formalin injected pawlicking events and the number of seconds each licking event lasts. These recordings are made for about 50 minutes after the formalin injection.

Several different scoring parameters have been reported for the formalin test. The total time spent licking and biting the injected paw is demonstrated to be most relevant (Coderre et al., Eur. J. Neurosci. 6; 1328–1334, 1993; Abbott et al., Pain, 60; 91–102, 1995) and may be chosen for the testing score. The early phase score is the sum of time spent licking, in seconds, from time 0 to 5 minutes. The late phase is scored in 5 minute blocks from 15 minutes to 40 minutes and is expressed accordingly or also by adding the total number of seconds spent licking from minute 15 to minute 40 of the observation period.

Data may be presented as means with standard errors of means (±SEM). Data may also be evaluated by one-way analysis of variance (ANOVA) and the appropriate contrasts analyzed by Dunnett "t" test for two sided comparisons. Differences are considered to be significant if, for example, the P-value is less than 0.05. Statistics may be determined at the 5 minute time point and at 5 minute intervals between 15 and 40 minutes. Where data are expressed as total amount of time spent licking in the late phase, statistics may be performed on the total time spent licking as well and may be indicated accordingly.

In addition to the Formalin Test, the well known Mouse Writhing Test, essentially as described in published International Application WO 00/028980, may also be employed to demonstrate the analgesic properties of compounds of the present invention.

Mouse Writhing Test

An accepted procedure for detecting and comparing the analgesic activity of different classes of analgesic drugs, for which there is a good correlation with human analgesic activity, is the prevention of acetic acid-induced writhing in mice. Mice are orally administered various doses of a test compound or placebo prior to testing. The mice are then injected intraperitoneally with acetic acid (0.55% solution, 10 mL/kg) five minutes prior to a designated observation period. Inhibition of writhing behavior is demonstrative of analgesic activity. Haubrich et al., "Pharmacology of pravadoline: a new analgesic agent", The Journal of Pharmacology and Experimental Therapeutics, 255 (1990) 511–522. For scoring purposes "writhe" is indicated by whole body stretching or contracting of the abdomen during an observation period beginning about five minutes after receiving the acetic acid.

$ED_{50}$ values, and their standard error of means (SEM), are determined using accepted numerical methods for all test compounds administered. For example, see R. E. Kirk (1982) "Experimental Design: Procedures for the behavioral sciences," 2nd ed. One method to establish the significance of the analgesic activity of a given test compound compared to that of another is to calculate the SEM values for each $ED_{50}$ value. If the SEM values do not overlap the line of addition, then the ED50 values are significantly different from the line of addition.

Yet another accepted animal model to demonstrate the ability of a particular compound to treat pain, or provide analgesic effects, is the well known Rat Model of Carrageenan-induced Thermal Hyperalgesia, also described in published International Application WO 00/028980.

Carrageenan-induced Thermal Hyperalgesia in Rats

Another accepted method for detecting and comparing the analgesic activity of different classes of analgesic compounds for which there is good correlation with human analgesic activity is the reversal of carrageenan-induced thermal hyperalgesia in rats (Hargreaves et al. *Pain* 32:77–88, 1988).

Rats are administered a dose test compound or vehicle and then injected subcutaneously into one hindpaw, with carrageenan (1.5% w/v, 100 μl). The response to noxious thermal stimulus is determined two hours later using a commercially available thermal plantar device (Ugo Basil, Italy) according to established methods (Hargreaves et al. *Pain* 32:77–88, 1988). Briefly, animals are habituated to a plastic behavioral enclosure for 5 min. A heat source is positioned directly beneath a hindpaw and the time taken for hindpaw withdrawal monitored automatically. If the animal does not respond within 20 sec, the stimulus is automatically terminated to prevent tissue damage. Measurements for both the injured and contralateral (control) hindpaw are recorded. Thermal hyperalgesia is evidenced by a shorter response latency by the injured as compared to the control paw. $ED_{50}$ values and their standard error of means (SEM) are determined using accepted numerical methods. For example, see R. E. Kirk (1982) "Experimental Design: Procedures for the behavioral sciences," 2nd ed.

We claim:

1. A compound of Formula:

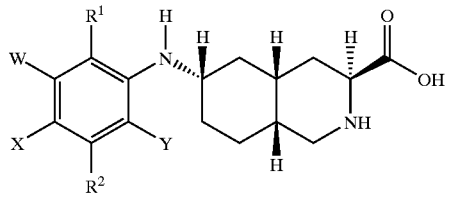

wherein $R^1$ is H, $CO_2H$, tetrazole, OH, or $(C_1-C_4)$alkyltetrazole;

$R^2$ is H, $(C_1-C_6)$alkyl, aryl, halo, $CO_2H$, $(C_1-C_6)$alkyl-heterocycle, $(C_1-C_6)$alkyl-(substituted)heterocycle, $(C_1-C_4)$alkyl-N—$SO_2$-aryl, $NO_2$, $NH_2$, $CF_3$, or $(C_1-C_6)$alkoxy carbonyl, $NSO_2$aryl;

W, X, and Y each independently represent H, $(C_1-C_6)$alkyl, $CO_2H$, halo, OH, heterocycle, substituted heterocycle, $CF_3$, $(CH_2)_nCO_2H$, $(C_1-C_6)$alkoxy, or $(C_1-C_6)$alkoxy carbonyl;

or optionally, X and $R^2$ together, along with the carbon atoms to which they are attached, form a fused-benzo group, or optionally, W and $R^1$ together, along with the carbon atoms to which they are attached, form a fused-benzo group or a fused-triazole group, and n is 0, 1, or 2;

or a pharmaceutically acceptable salt.

2. The compound according to claim 1 wherein W represents hydrogen.

3. The compound according to claim 1 wherein X represents hydrogen.

4. The compound according to claim 1 wherein Y represents hydrogen.

5. The compound according to claim 1 wherein $R^2$ represents hydrogen.

6. The compound according to claim 1 wherein $R^1$ represents tetrazole.

7. The compound according to claim 6 wherein X and Y represent hydrogen.

8. The compound according to claim 7 wherein $R^2$ represents hydrogen.

9. The compound according to claim 8 wherein W represents hydrogen.

10. A compound which is (3S, 4aR, 6S, 8aR) 6-(2-(1(2)H-tetrazol-5-yl)-phenylamino)-1,2,3,4,4a, 5,6,7,8,8a-decahydroisoquinoline-3-carboxylic acid or a pharmaceutically acceptable salt or prodrug thereof.

11. The compound according to claim 10 wherein the pharmaceutically acceptable salt is the dihydrochloride salt.

12. The compound according to claim 8 wherein W represents $C_1-C_6$alkyl.

13. The compound according to claim 12 wherein W represents Me.

14. A compound which is (3S, 4aR, 6S, 8aR) 6-(3-methyl-2-(1(2)H-tetrazol-5-yl)-phenylamino)-1,2,3,4,4a,5,6,7,8,8a-decahydroisoquinoline-3-carboxylic acid or a pharmaceutically acceptable salt or prodrug thereof.

15. The compound according to claim 14 wherein the pharmaceutically acceptable salt is the dihydroiodide salt.

16. The compound according to claim 14 wherein the pharmaceutically acceptable salt is the dihydrochloride salt.

17. The compound according to claim 8 wherein W is Halo.

18. The compound according to claim 17 wherein W is Cl.

19. A compound which is (3S, 4aR, 6S, 8aR) 6-(3-chloro-2-(1(2)H-tetrazol-5-yl)-phenylamino)-1,2,3,4,4a,5,6,7,8,8a-decahydroisoquinoline-3-carboxylic acid or a pharmaceutically acceptable salt or prodrug thereof.

20. The compound according to claim 19 wherein the pharmaceutically acceptable salt is the dihydroiodide salt.

21. The compound according to claim 19 wherein the pharmaceutically acceptable salt is the dihydrochloride salt.

22. A compound of the Formula:

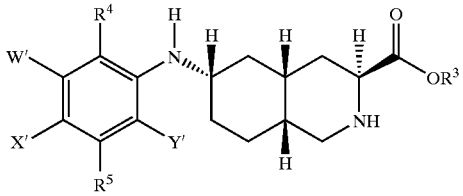

wherein $R^3$ is hydrogen, $(C_1-C_{20})$alkyl, $(C_2-C_6)$alkenyl, $(C_1-C_6)$alkylaryl, $(C_1-C_6)$alkyl $(C_3-C_{10})$cycloalkyl, $(C_1-C_6)$alkyl-N,N—$C_1-C_6$ dialkylamine, $(C_1-C_6)$alkyl-pyrrolidine, $(C_1-C_6)$alkyl-piperidine, or $(C_1-C_6)$alkyl-morpholine;

$R^4$ is H, $CO_2R^6$, tetrazole, OH, or $(C_1-C_4)$alkyltetrazole;

$R^5$ is H, $(C_1-C_6)$alkyl, aryl, halo, $CO_2R^7$, $(C_1-C_6)$alkyl-heterocycle, $(C_1-C_6)$alkyl-(substituted)heterocycle, $(C_1-C_4)$alkyl-N—$SO_2$-aryl, $NO_2$, $NH_2$, $CF_3$, or $(C_1-C_6)$alkoxy carbonyl, $NSO_2$aryl;

W', X', and Y' each independently represent H, $(C_1-C_6)$alkyl, $CO_2R^8$, halo, OH, heterocycle, substituted heterocycle, $CF_3$, $(CH_2)nCO_2R^8$, $(C_1-C_6)$alkoxy, or $(C_1-C_6)$alkoxy carbonyl;

$R^6$, $R^7$, and $R^8$ each independently represent hydrogen, $(C_1-C_{20})$alkyl, $(C_2-C_6)$alkenyl, $(C_1-C_6)$alkylaryl, $(C_1-C_6)$alkyl $(C_3-C_{10})$cycloalkyl, $(C_1-C_6)$alkyl-N, N—$C_1-C_6$ dialkylamine, $(C_1-C_6)$alkyl-pyrrolidine, $(C_1-C_6)$alkyl-piperidine, or $(C_1-C_6)$alkyl-morpholine;

or optionally, X' and $R^5$ together, along with the carbon atoms to which they are attached, form a benzo-fused group, or optionally, W' and $R^4$ together, along with the carbon atoms to which they are attached, form a benzo-fused group or a triazole-fused group, n is 0, 1, or 2;

with the proviso that where $R^4$ is $CO_2R^6$, or $R^5$ is $CO_2$ or W', X', or Y' is $CO_2R^8$ then at least one, but no more than two of $R^3$, $R^6$, $R^7$, and $R^8$ is other than hydrogen;

or a pharmaceutically acceptable salt thereof.

23. The compound according to claim 22 wherein $R^3$ is $C_1$–$C_{20}$ alkyl.

24. The compound according to claim 23 wherein $R^3$ is $C_1$–$C_6$ alkyl.

25. The compound according to claim 24 wherein $R^4$ is tetrazole.

26. The compound according to claim 25 wherein $R^5$ is hydrogen.

27. The compound according to claim 26 wherein X' and Y' are hydrogen.

28. The compound according to claim 27 wherein W' is hydrogen.

29. A compound which is 2-ethyl-butyl (3S, 4aR, 6S, 8aR) 6-(2-(1(2)H-tetrazol-5-yl)-phenylamino)-1,2,3,4,4a,5,6,7,8,8a-decahydroisoquinoline-3-carboxylate, or a pharmaceutically acceptable salt thereof.

30. The compound according to claim 29 wherein the pharmaceutically acceptable salt is the dihydrochloride salt.

31. The compound according to claim 27 wherein W' is $C_1$–$C_6$ alkyl.

32. The compound according to claim 31 wherein W' is Me.

33. A compound which is 2-ethyl-butyl (3S, 4aR, 6S, 8aR) 6-(3-methyl-2-(1(2)H-tetrazol-5-yl)-phenylamino)-1,2,3,4,4a,5,6,7,8,8a-decahydroisoquinoline-3-carboxylate, or a pharmaceutically acceptable salt thereof.

34. The compound according to claim 33 wherein the pharmaceutically acceptable salt is the dihydroiodide salt.

35. The compound according to claim 33 wherein the pharmaceutically acceptable salt is the dihydrochloride salt.

36. The compound according to claim 27 wherein W' is Halo.

37. The compound according to claim 36 wherein W' is Cl.

38. A compound which is 2-ethyl-butyl (3S, 4aR, 6S, 8aR) 6-(3-chloro-2-(1(2)H-tetrazol-5-yl)-phenylamino)-1,2,3,4,4a,5,6,7,8,8a-decahydroisoquinoline-3-carboxylate or a pharmaceutically acceptable salt thereof.

39. The compound according to claim 38 wherein the pharmaceutically acceptable salt is the dihydroiodide salt.

40. The compound according to claim 39 wherein the pharmaceutically acceptable salt is the dihydrochloride salt.

41. A method of treating a neurological disorder or neurodegenerative disease selected from the group consisting of headache, cluster headache, tension-type headache, chronic daily headache, acute pain, chronic pain, severe pain, intractable pain, neuropathic pain, post-traumatic pain, and migraine, which comprises administering to a patient in need thereof an effective amount of a compound according to claim 1.

42. A method of treating a neurological disorder or neurodegenerative disease selected from the group consisting of headache, cluster headache, tension-type headache, chronic daily headache, acute pain, chronic pain, severe pain, intractable pain, neuropathic pain, post-traumatic pain, and migraine, which comprises administering to a patient in need thereof an effective amount of a compound according to claim 22.

43. A pharmaceutical composition comprising an effective amount of the compound according to claim 1, in combination with a pharmaceutically acceptable carrier, diluent, or excipient.

44. A pharmaceutical composition comprising an effective amount of the compound according to claim 22, in combination with a pharmaceutically acceptable carrier, diluent, or excipient.

* * * * *